United States Patent [19]

Thurston

[11] Patent Number: 4,523,822

[45] Date of Patent: Jun. 18, 1985

[54] REFRACTOR WITH OPTICALLY ENCODED CYLINDER AXIS POSITION

[75] Inventor: Marlin O. Thurston, Columbus, Ohio

[73] Assignee: R. H. Burton Company, Grove City, Ohio

[21] Appl. No.: 513,707

[22] Filed: Jul. 14, 1983

[51] Int. Cl.³ .............................................. A61B 3/02
[52] U.S. Cl. .................................... 351/234; 351/235
[58] Field of Search ................................ 351/234, 235

[56] References Cited

U.S. PATENT DOCUMENTS

| | | |
|---|---|---|
| 2,293,200 | 2/1960 | Wright . |
| 2,938,426 | 5/1960 | Armbuster et al. . |
| 2,968,213 | 1/1961 | Wright et al. . |
| 2,995,065 | 8/1961 | Wright et al. . |
| 3,498,699 | 3/1970 | Wilkinson . |
| 3,860,300 | 1/1975 | Persson . |
| 3,969,020 | 7/1976 | Lynn et al. . |
| 4,185,986 | 1/1980 | Buhler . |
| 4,385,813 | 5/1983 | Klein et al. ........................ 351/235 |
| 4,426,140 | 1/1984 | Stephens ............................ 351/235 |

Primary Examiner—Rodney B. Bovernick
Attorney, Agent, or Firm—Mueller and Smith

[57] ABSTRACT

An ophthalmic refractor is provided which is configured for carrying out the Jackson cross-cylinder test. To improve accuracy, an optical encoder is provided in conjunction with each cylinder axis control knob and in conjunction with the lens mount of the cross-cylinder test lens. The cross-cylinder test lens is driven by a d.c. motor and worm gear assembly and a control circuit is provided for selectively energizing the drive motor in correspondence with the settings of the optical encoders. For power mode operation, the control circuit effects motor drive to align the axes of the cross-cylinder lens and pertinent cylinder axis. Correspondingly, for axis mode operation, the control circuit further adjusts the positioning by the motor of the cross-cylinder lens by 45°. Illuminated digital displays are provided on the refractor for direct digital readout of cylinder axis diagnostic data as well as test mode identification.

20 Claims, 15 Drawing Figures

REFRACTOR WITH OPTICALLY ENCODED CYLINDER AXIS POSITION

BACKGROUND

Correction of defective human visual perception is centered in general upon clinical refraction, an approach based upon optics, physiology and the psychology of perception. Generally, any refractive analysis of human vision has some basis in optics. For example, the treatment of defective vision will analyze the position of focus of the eye which may be displaced from the emmetropic retina under conditions of either myopia or hyperopia. In addition, the eye may be astigmatic, exhibiting different focal aspects for each primary meridian which, in turn, may be oriented anywhere within a 180° aspect. Thus, the clinician is often called upon to approach the optical subject matter of diagnosis by evaluating the dioptric aspects of focal difficiency as they may be related to meridial power variances. The correction of ocular astigmatism is carried out by collapsing the interval of Sturm with cylinder lenses. See the following publication in this regard:

I. "Visual Optics and Refraction-a Clinical Approach" by D. D. Michaels, second edition, C. V. Mosby Company, St. Louis 1980.

Commonly, an opthalmic instrument referred to as a refractor is employed for efficiently carrying out optical analysis. Refractors typically are fashioned comprising right and left batteries, each having an eye position for the patient before which any of a broad variety of disk mounted testing lenses may be positioned. These lenses may be spherical, exhibiting a broad range of powers, or cylindrical, again exhibiting power variations but with respect to alignment along plus and minus axes.

Investigations of techniques for carrying out ophthalmic evaluation of the astigmatic eye have evolved a variety of analytic approaches. Linksz has described a method for determining meridial orientation, i.e. "checking cylinder for axis and amount" by rotating a correcting cylinder before the eye. This method analyzes the eye with a cylinder lens and considers the principle that if two cylinders are juxtaposed such that their axes do not coincide, a set of optical resultants is produced creating new cylindrical powers and axes. By selecting the correcting cylinder as opposite in power to the eye cylinder, it becomes possible to determine the axial orientation of the eye cylinder and the dioptic power aspects thereof by a progressive error evaluation carried out by manipulating the correcting cylinder. See the following publication in this regard:

II. Linksz, A.: Determination of Axis and Amount of Astigmatic Error by Rotation of Trial Cylinder. Archives of Ophthalmology, October, 1942.

The rotating cylinder approach to analysis was further developed by the Jackson cross-cylinder technique wherein the above-noted resultant cylinder developed from the utilization of two cylinders off axis is further contrasted against a third sphero-cylindrical combination. For a more detailed discussion of this clinical approach, reference is made to the following publications:

III. "Clinical Refraction" by I. M. Borish, second edition, The Professional Press, Inc., Chicago, Ill.

IV. Jackson, E.: The Astigmic Lens (Crossed Cylinder). Reprinted in Opt. Devel. August, 1932.

The Jackson cross-cylinder test has been recognized as most beneficial to analysis and has been implemented broadly in ophthalmic refractors. Generally, the test is carried out in two stages. Initially, an objective evaluation is made of the eye, typically employing retinoscopy procedures which may be further modified using an astigmatic chart test to develop a first approximation of cylinder power and axis. Following this first approximation, the resultant data then are used to develop the subjective, cross-cylinder test which is carried out with the refractor to achieve a refined analysis. The test is carried out in both a cylinder axis and cylinder power mode, most practitioners preferring to carry out the former mode initially. Under the test procedure, the patient is seated in a darkened examination room before the refractor and is asked to observe an illuminated distant target. The correcting cylinder axis before an appropriate eye then is manipulated by manually turning an axis control knob which is operated in conjunction with two complementary large surrounding protractor scales. Such manipulation adjusts the position of the axis of the pertinent test cylinder and its orientation is read at the scale in degrees ranging from 0 degrees to 180 degrees. Typically the graduations of the scales are arranged in steps of 5 degrees. It is from this scale that the ultimate axis information is read out for prescription purposes.

Upon the axis control knob being adjusted to the first approximation a cross cylinder, provided as a lens consisting of equal power plus and minus cylinders with their axes 90° apart is positioned at the eye station. This test lens is mounted in its loupe for rotation about a "flip" axis midway between the plus and minus axes. When the lens is flipped, the plus and minus axes change places. For axis mode testing, the cross cylinder also is positioned with respect to the noted first approximation such that its axis is oriented 45° with respect to the correcting cylinder axis. Such aligning procedure is carried out somewhat semi-automatically. Generally, the refractor will carry the cross cylinder lens within a turret which is manually rotated to position the lens before the eye station or tube. The turret carrying the cross-axis lens, also includes a knurled knob arrangement wherein the operator may readily flip the lens between its above-noted positions. To carry out the initial alignment of the cross-axis lens with respect to the axial orientation of the correcting cylinder lens then before the patients eye, a multiple gear assemblage within the turret which is structured such that by turning the axis control knob, the cross-cylinder lens is synchronously manipulated in a manner wherein its minus axis is aligned with the corresponding correcting cross-cylinder axis. To aid the operator, spaced pairs of red and white dots are positioned upon the cross-cylinder lens to respectively show the location of the minus and plus power axes. To move the cross cylinder to its appropriate orientation for an axis mode test, the operator further rotates the cross cylinder to a mechanical detent controlled orientation to effect a 45° displacement. One technique for assuring the operator that the cross cylinder is in a proper orientation for the axis mode check is an observation of the knurled flip knob position as corresponding to the axis of the correcting cylinder. With the above adjustments carried out, the cross cylinder lens is "flipped" from its first position to the alternate transverse position by rotating the knurled knob with the thumb. The patient then is asked which position is better and depending upon the response and assuming testing is carried out with minus cylinder lenses, the correcting cylinder axis knob is manipulated to rotate the correcting cylinder toward the position of the red dots at which vision is improved. These steps are repeated until a final end point is reached such that when the cross cylinder is flipped from one position to the other, the patient's vision is equally blurred. The operator then records the reading of the axis control knob by observing a painted line indicia thereon as it is positioned adjacent to a line of the earlier-described scale. Generally, the operator interpolates the axial orientation in degrees within given 5 degree steps of the scale.

Following the axis mode check, the cross-cylinder lens is rotated by the operator 45° to another mechanical detent controlled position for carrying out a cylinder power mode check. Visual confirmation of the appropriate position for the cross-cylinder lens usually is provided by noting the position of the earlier-described red dots as being parallel to the correcting cylinder minus axis. As the patient monocularly fixates upon the illuminated target, the cross cylinder lens is flipped between alternate positions and the patient is asked, as before, at which position vision is better or worse. If vision is less blurred with the red dots parallel to the minus correcting cylinder axis, correcting minus cylinder power is increased. If vision is better with the red dots perpendicular to the minus correcting cylinder axis, the correcting cylinder power is reduced. Finally, an end-point is obtained wherein correcting cylinder power is correct and the vision of the patient equally is impaired when the cross-cylinder lens is flipped between its alternate positions. With completion of the test in both the cylinder axis and cylinder power modes, the cross-cylinder test procedure is completed. This test is carried out in both modes usually for both eyes of the patient commencing with the right eye.

While industry has endeavored to achieve a high quality of performance for ophthalmic refractors and has striven to minimize the opportunities for operator error in utilizing the devices, improvement in overall diagnostic accuracy on the part of the instruments still is needed. The synchronization of axial orientations between the correcting cylinder lens and the cross-cylinder lens involves a gear train drive which inherently exhibits backlash charactertistics. These backlash characteristics have been observed to generate errors in synchronization between the correcting lens and the cross-cylinder lens typically on the order of 3° and, on occasions, to the extent of about five degrees. The gear train associating these lenses is subjected to operator imposed torques and forces in consequence both of the initial manual maneuvering of the cross-cylinder lens carrying turret into its operative position as well as by the subsequent manipulations of the lens into its 45° detent position for axial mode performance. Commonly, the lubricant within the gear structures dries to alter its viscosity, dirt and lint are "picked up" within the trains and bearing surfaces to engender maneuvering error. Such environmental and use related conditions lead to inaccurate preliminary lens settings. Further, in flipping the cross-cylinder lens by thumb actuation of the knurled knobs from which it is pivotally driven a torque again may be observed to be induced into the gear structured mounting. As the instruments age and are used, such action also can alter the axis position otherwise established by the detent effecting turret alignment. Thus the errors in synchronization are compounded by forces exerted at either end of the synchronizing gear chain, ie. from the axis control knob and from the cross cylinder lens loupe itself. The errors thus occasioned in the typical use of refractors, of course, are translated into prescription error. It may be noted that particularly where cylinder axis power as is required by the patient becomes higher then the criticality of proper axial readout correspondingly becomes elevated.

While the utilization of relatively broad, five degrees increments typically in conjunction with the protractor scale associated with the axis control knob may be appropriate when considering the amount of inherent error due to gear train backlash, the operator further is called upon to read this rather broad incremental scale in the darkened environment of an examination room. This further leads to potential operator error both in the direct readout and in the attempt to interpolate between five degrees spaced indicia. The darkened environment as well as potential operator fatigue also may lead to error in carrying out the proper adjustment of the cross cylinder lens. For example, the operator must recall that the lens is to have one orientation for axis mode performance and must then be rotated to a second 45° displaced orientation for cylinder power mode testing. Where the operator forgets this manipulation or fails to properly read printed indicia or respond to the orientations of the red and white dots on the cross-cylinder lens in the darkened environment, then important error ensues in diagnostic testing.

SUMMARY

The present invention is addressed to an ophthalmic refractor with which the practitioner may carry out the Jackson cross-cylinder test with improved accuracy and reliability. Through the employment of absolute position encoding techniques in conjunction with the axis defining orientation of the cylindrical axis control knob and associated cross-cylinder lens assembly of a refractor, improvement of testing is achieved both in terms of reliability and accuracy of axis data readout. Accurate cylinder axis readout for prescriptive purposes is achieved with at least one degree of definition without resort to the interpolation of relatively broad dial indicia and printed scale positions. By combining the absolute position encoding arrangement of the invention in conjunction with a small electric motor drive for the cross-cylinder lens of each refractor battery, the accuracy of cross-cylinder lens positioning is improved and the discrepancies otherwise occasioned from multigear backlash characteristics and the like essentially are eliminated. Further, power and axis mode components of the Jackson cross-cylinder test are carried out with more reliability through an automatic axial displacement of the cross-cylinder lens through 45° for axis mode testing. The particular mode of a given test is readily apparent to the practitioner through the use of an illuminated display in conjunction with a mode selection switch coupled with each battery of the refractor. The reliability of readout of axis information as well as test mode selection is provided through the use of illuminated displays for such information, the displays being provided in digital form as, for example, multisegment light emitting diode digit formation. In a preferred embodiment, the cross-cylinder lens is mounted for hand manipulated rotation about its flip axis, a procedure which has been provided in conjunction with earlier refractors with which the practitioner will have been familiar. Through the use of the noted motor drive in conjunction with a worm gear connection with the cross-cylinder lens mounting, forces occasioned from the thrust associated with flipping the cross-cylinder lens are fully resisted to assure no maladjustment to the axis setting.

Another object of the invention is to provide the above cataloged improvements in accuracy and reliability of refractor factor usage in conjunction with the Jackson cross-cylinder test while maintaining those aspects of the refractor with which the practitioner may have been familiar over extended periods of practice. Thus, the improvements in performance of the instrument are achieved in conjunction with a maintenance of the confidence which the practitioner may have due to a familiarity with the physical aspects of the refractor itself.

Another feature and object of the invention is to provide a refractor which incorporates a housing having a patient eye position for viewing along a sight axis which is extensible through the housing. A cylinder lens assembly is positioned within the housing which includes a plurality of rotatably movable cylinder lens components. These components are mounted such that they may be positioned such that a select cylinder lens component is moved into an aligned orientation with the noted sight axis. A hand manipulated axis control knob is engagable with a position cylinder lens for effecting the rotation thereof to a select cylinder axis rotation and a first code carrier is mounted upon the housing for movement with the manipulated axis control knob. A first position encoder responsive to axis control knob positions is provided for deriving a unique first position signal corresponding substantially with the instantaneous cylinder axis orientation of the positioned cylinder lens. Within the housing there also is provided a cross-cylinder assembly having a cross-cylinder arrangement with selected power axis, a rotatable lens mount supporting the cross-cylinder lens arrangement which is movable to a position wherein the cross-cylinder lens is in alignment with the noted sight axis. A motor arrangement is mounted with the housing having an output coupled in driving relationship with the rotatable lens mount and which is energizable in response to a drive signal to effect rotation of the mount. A second position encoding arrangement is mounted with the housing which is responsive to the rotational orientation of the lens mount for deriving a unique second position signal. A digital readout is provided which responds to a digital readout signal to display numeric values. A control circuit is provided which responds to the first position signal to derive a digital readout signal. The circuit further responds to the first position signal and the second position signal in the presence of an axis mode condition for deriving a drive signal effecting the driven movement of the lens mount positioning the cross-cylinder select axis in an orientation displaced 45° from the cylinder lens axis and the control circuit further is responsive to the first position signal and the second position signal in the presence of a power mode condition for deriving a drive signal effecting the driven movement of the lens mount to position the cross-cylinder lens arrangement power axis in alignment with the cylinder axis.

As another object of the invention, a refractor is provided which includes a battery having a patient eye position aligned along a sight axis which is extensible through the battery. A cylinder lens assembly is provided within the battery including a plurality of rotatable cylinder lenses each having cylinder axis. An arrangement is provided for positioning a selected cylinder lens in alignment with the sight axis and an axis control rotatable to select positions is provided for setting the cylinder axis of a selected cylinder lens. A first code carrier is provided which is mounted for movement with the axis control. A first readout arrangement is responsive to the code carrier for deriving a unique first position signal substantially for each cylindrical axis setting. A cross-cylinder assembly is mounted upon the battery which includes a cross-cylinder lens having mutually perpendicular power axes, a rotatable lens mount selectively positionable into an aligned orientation with the sight axis, a flip mount supporting the cross-cylinder upon the rotatable lens mount for pivotal movement about a flip axis disposed intermediate the perpendicular power axes, a motor having an output coupled in driving relationship with the rotatable lens mount and which is energizable in response to a drive signal to effect the rotation of the lens mount. A second code carrier is mounted for movement upon the battery with the rotatable lens mount and a second readout is provided for deriving a unique second position signal of predetermined relationship substantially with the instantaneous position of the cross-cylinder lens power axes. A digital readout is provided which is responsive to a digital input signal for displaying a numeric value corresponding therewith and which is visually perceptible in the presence of low ambient illumination. A mode switch is provided which is selectively actuable to provide an axis mode condition and a power mode condition, and a control circuit is provided which responds to the first position signal for deriving the digital input signal to effect the digital readout display and which further is responsive to the first position signal and the second position signal in the presence of the axis mode condition for deriving a drive signal until the cross cylinder lens flip axis is located parallel with the position cylinder lens component cylinder axis. The circuit is further responsive to the first position signal and the second position signal in the presence of the power mode condition for deriving a drive signal until a selected cross-cylinder lens power axis is located parallel with the position cylinder lens component cylinder axis.

Other objects of the invention will, in part, be obvious and will, in part, appear hereinafter. The invention, accordingly, comprises the system and apparatus possessing the construction, combination of elements and arrangement of parts which are exemplified in the following Detailed Description. For a fuller understanding of the nature and objects of the invention, reference should be had to the following Detailed Description taken in connection with the accompanying drawings.

DETAILED DESCRIPTION

Figure 1:
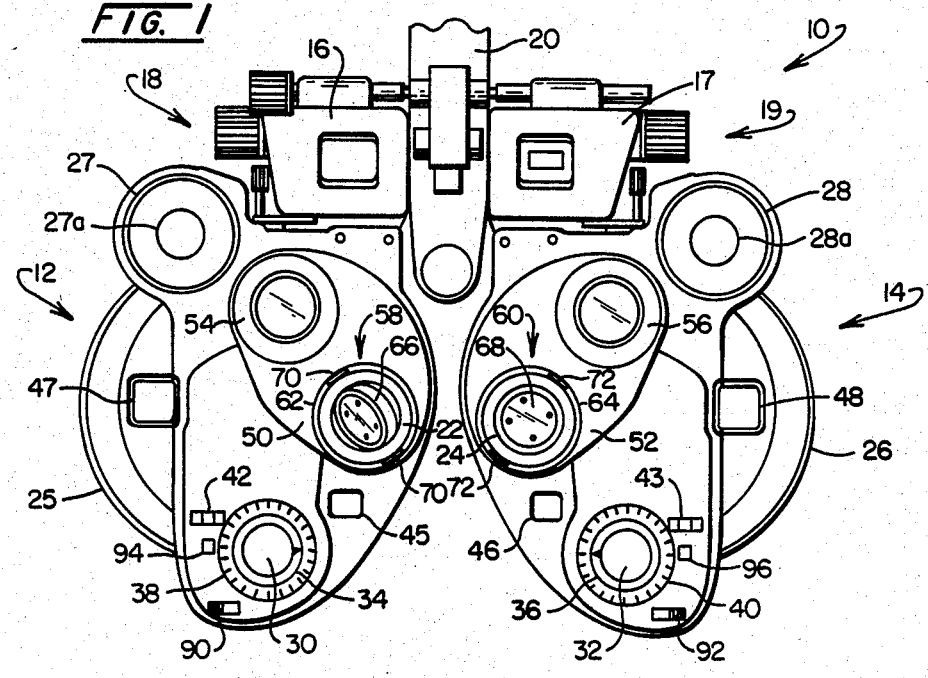
FIG. 1 is a front view of a refractor structured in accordance with the invention.

The housing for a refractor structured in accordance with the instant invention bears a close similarity to refractors which have been utilized by practitioners over a considerable period of time. Thus, while incorporating features permitting higher accuracy and reliability, the device as so structured enjoys an advantageous familiarity or the practitioner with respect to its use and inculcates a continued confidence in its utility for providing optimum services to the patient. Referring to FIG. 1, a refractor is depicted generally at 10 as is observed typically from a practitioner's position is seen to include two substantially identical batteries, a right eye battery being represented at 12 and a left eye battery being represented at 14. These batteries 12 and 14 are supported by a bridging structure having components represented generally at 16 and 17 which, in turn, are connected with a yoke type assembly 20 which extends to a refractor arm (not shown), in turn, supported by an ophthalmic instrument stand (not shown). Various eye span and leveling adjustments are provided within the support components 16 and 17 to accommodate for individual patients. For example, leveling and interpupillary adjustment knobs are provided for each of the batteries 12 and 14 as represented, respectively at 18 and 19. As is described in detail, for example, in U.S. Pat. No. 3,498,699, each battery of the refractor 10 carries a collection of lenses which are supported within rotatable disks which the practitioner may position in alignment with viewing tubes at which the patients' eye is positioned. These viewing tubes represent the sight axis for the testing system and are located at 22 in battery 12 and at 24 in battery 14.

Each of the batteries contains a plurality of spherical lenses which conventionally are mounted about the periphery of an annular disk which may be rotated so as to position selected lenses before viewing tubes 22 and 24. In this regard, a knurled outer portion 25 of one such disk is provided for maneuvering spherical lenses in battery 12, while a similar peripheral edge is provided at 26 in battery 14. Additionally, a strong sphere lens control knob is provided for batteries 12 and 14, respectively at 27 and 28. Positioned coaxially upon each of these control knobs 27 and 28 there may be provided an auxiliary lens control knob as shown at 27a and 28a. Each of the batteries also contains a cylinder lens assembly formed of two disks, one such disk carrying a stronger collection of cylinder lenses about its periphery, and the other carrying a collection of weaker cylinder lenses such that they may be combined in a progressive power sequence through interconnection with a Geneva intermittent drive. The latter drive is manipulated by a control knob as shown at 30 on battery 12 and at 32 on battery 14. While control knobs 30 and 32 serve to position successive cylinder lenses before respective viewing tubes 22 and 24, the cylinder axis for each such positioned cylinder lens may be controlled by rotative manipulation of an axis control knob 34 at battery 12 and 36 at battery 14. Power readouts identifying the cylinder lenses of the associated disk assembly are set forth in numeric fashion at windows 45 and 46, while spherical readouts are provided at windows 47 and 48 of respective batteries 12 and 14. Thus, as the patient observes an illuminated distant target through either of the viewing tubes 22 or 24, the practitioner may manipulate the associated axis control knob 34 or 36 to adjust the orientation of the cylinder axis of the cylinder lens then before the viewing tube. Additionally, cylinder power control knobs 30 and 32 may be manipulated. A protractor-type scale as at 38 on battery 12 and 40 on battery 14 is provided which carries indicia in degrees from 0 to 180 which may be read in conjunction with a pointer on respective axis control knobs 34 and 36 to show the axis orientation of the cylinder lens at the viewing tubes. For the instant purpose, this scale is provided merely for the convenience of the operator, its presence being somewhat redundant. Accordingly, the scales are graduated in broad, 15° increments of axis orientation. However, in the past, such scales were graduated in five degree increments to show the position of cylinder lens axis at the viewing tube. Control of the axis orientation of these cylinder lenses is by a sun-planet type gear association in typical refractor designs.

The cylinder lens axis orientation otherwise determined by the practitioner from scales 38 and 40 is replaced with the instant refractor by a solid-state illuminated three digit readout at displays 42 and 43 in respective batteries 12 and 14. The digits of these readouts may be provided as multi-segment LEDs which when energized are readily perceived by the practitioner even though operating in the low ambient lighting environment required to carry out clinical refraction. In the past, errors have been observed in interpolating the earlier five degree increments of axis orientation provided by scales read in conjunction with the axis control knobs. The instant refractor 10 will be seen to provide accurate readouts readily within one degree increments without interpolation.

The above described Jackson cross-cylinder test conventionally carried out using a cross-cylinder lens mounted upon a rotative lens mount which, in turn, is supported upon a pivotal bi-loupe turret. One such turret is pivotally mounted on each battery of the refractor in a manner such that the practitioner rotates the turret to an orientation wherein the cross-cylinder lens is aligned with an associated battery viewing tube. FIG. 1 shows a turret 50 pivotally mounted upon battery 12 and a corresponding turret 52 mounted upon battery 14. Turrets 50 and 52 each support a rotary prism lens system shown respectively at 54 and 56, as well as a cross-cylinder assembly as shown, respectively, at 58 and 60. In conventional fashion, each of the assemblies 58 and 60 includes a rotatable lens mount shown, respectively, at 62 and 64 which supports a cross-cylinder lens as shown, respectively, at 66 and 68. Cross-cylinder lenses 66 and 68 may be pivotally rotated about a flip axis by the manual movement of a pivoting assembly extending to oppositely disposed knurled knobs as shown at 70 in conjunction with lens 66 and at 72 in conjunction with lens 68. FIG. 1 shows that cross-cylinder lens 66 is in an orientation wherein it is being rotated or pivoted about its flip axis. In the past, the axial orientation of the cross-cylinder lens as at 66 was synchronized with the cylinder axis positioned before an associated viewing tube as at 22 by virtue of a geared connection of both with axis control knob 34, it being understood that a similar arrangement was provided in conjunction with control knob 36 and cross-cylinder lens 68. Generally, about six gears have been utilized in providing for this synchronized drive provided to the cross-cylinder lens mount and such arrangement has resulted in error occasioned by the inherent backlash characteristics of the multi-geared association.

Figure 2:
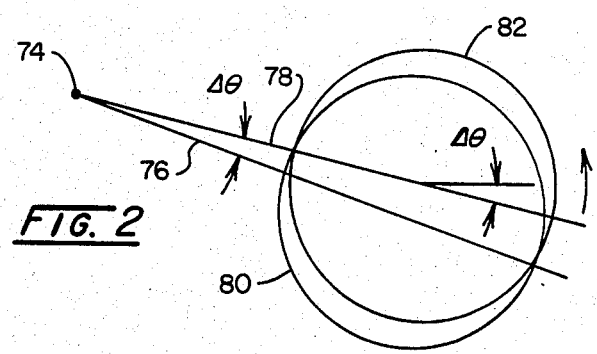
FIG. 2 is a schematic representation of the degree of error development characteristic of refractor devices of the prior art.

The amount of error which may be associated with an all mechanical system of the past not only involves inherent backlash characteristics but also is occasioned by the arrangement wherein the lens carrying turret as at 50 or 52 is pivotally maneuvered into an operational orientation as shown in FIG. 1. Inasmuch as a detent or stop is required to effect a proper positioning of these turrets, an error in cross-cylinder lens axial orientation also will evolve from turret positioning variations. In effect then, the error of backlash inherent in the gear train is cumulative with the error associated with turret positioning. Looking additionally to FIG. 2, the error due to turret positioning is represented in diagrammatic form. In the figure, a turret pivot point is represented at 74 and an axis from that point to the cross-cylinder lens center for a perfect turret alignment is represented by line 76. Where turret alignment is not proper, the axis 76 is pivoted, for example to the error axis represented by line 78 and the angle of error therebetween becomes $\Delta\theta$. The earlier gear train association between the axis control knob and the rotatable cross-cylinder mount is made with respect to the turret position. Thus, the cross-cylinder lens is moved from the orientation represented by circular profile 80 to that represented at circle 82 and the error $\Delta\theta$ then is compounded by the gear train performance to result in an angle error of $2\Delta\theta$. The resultant axial error is undesirable, particularly when patient eye corrections involving higher magnitudes of cylindrical power are involved.

Returning to FIG. 1, it may be appreciated that not only does the manual manuevering of the turrets as at 50 and 52 generate error due to the mechanical wear induced variations which may occur in detents or stops involved in their mechanical positioning, but also the backlash characteristics of the gear train adjusting the angular orientation of the cross cylinder lenses may be amplified due to the thrust imposed into the gear train by virtue of the manual manipulation or flipping of the cross-axis lenses as at 66 and 68 through the associated knurled knobs shown, respectively, at 70 and 72. As noted above, the errors can reach levels as high as 5° and are typically in the range of about 3° representing an undesirable inaccuracy. Of course, such inherent inaccuracies may justify the use of relatively broad incrementations of 5°, for example, in providing a prescription readout from the scales as earlier provided at the locations described in conjunction with scales 38 and 40.

Returning to FIG. 1, in accordance with the present invention, the particular axis or power mode utilized for the cross-cylinder testing procedures is selected by the practitioner utilizing a slide switch mounted upon each battery 12 and 14 as shown, respectively, at 90 and 92. The orientation of these switches 90 and 92 is positively represented by illuminated mode displays shown, respectively, at 94 and 96. For example, the display provided at 94 and 96 may be a typical seven segment light emitting diode which is energized to show an "A" for axis mode operation and, correspondingly, a "P" for power mode operation.

With respect to the operation of instrument 10 in either an axis or power mode, the same cross-cylinder structural assembly is utilized but under different test mode criteria.

Figure 3:
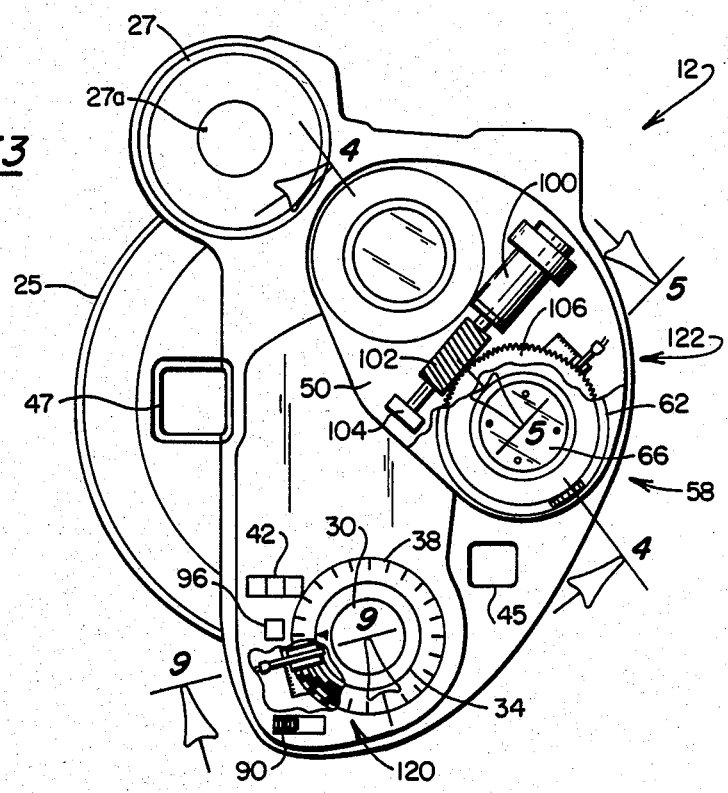
FIG. 3 is a partial front view of the refractor of FIG. 1 with portions broken away to reveal internal structure.
Figure 4:
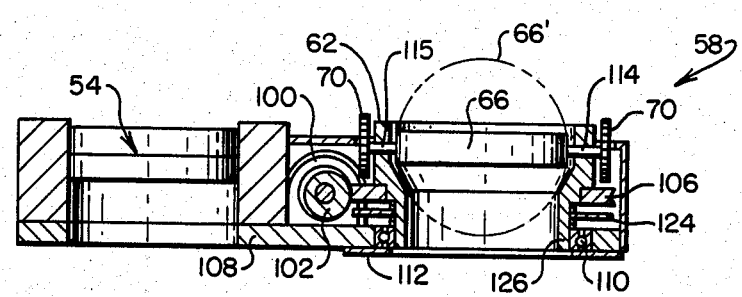
FIG. 4 is a partial sectional view taken through the section 4—4 shown in FIG. 3.
Figure 5:
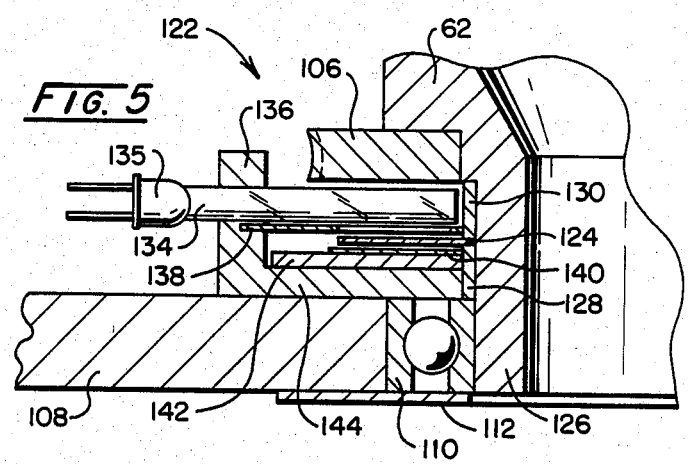
FIG. 5 is a partial sectional view taken through the plane 5—5 shown in FIG. 3.

Referring to FIGS. 3, 4 and 5, the structuring of the cross-cylinder axis assembly in accordance with the invention is revealed. In the discourse to follow, the description of the assembly is made in conjunction with the components of battery 12. It should be understood, however, that the description also applies to the components of battery 14. As noted above, for the preferred embodiment, the cross-cylinder lens arrangement utilizes a singular lens which is "flipped" by the practitioner in the course of carrying out a test. Accordingly, a singular cross-cylinder lens is provided which is structured in conventional fashion, for example, having 0.25-diopter cylinders with the the respective principal axes thereof oriented 90° apart. One of these cylinders is positive and the other negative and they are mounted such that the flip axis, represented by the rotational axis of the flip mount extending between knurled knobs 70, is midway between these two principal axes or located 45° from either. The practitioner long has been afforded the opportunity of identifying the position of these axes by small, spaced red and white dots impressed upon the cross-cylinder lenses themselves. As shown in larger scale in FIG. 3, the minus axis of lens 66 is shown by spaced solid dots representing the earlier red dots and the positive axis is identified by spaced circles repesenting the conventional white dots. In carrying out the Jackson cross-cylinder test with the refractor 10, the synchronized movement of the rotatable cross-cylinder lens mount as at 62 for battery 12 is provided by drive from a PM electric motor 100 mounted upon turret 50 and having an output connected in driving relationship with a worm drive 102. In this regard, the output shaft of motor 100 is coupled to worm drive 102 which is provided a shaft extension supported rotatably upon a shaft bearing 104. Worm gear 102, in turn, is enmeshed in driving relationship with the teeth of a ring shaped worm gear 106 which, as revealed in FIGS. 4 and 5, extends from the cylindrical rotatable lens mount 62. Concerning mount 62, FIGS. 4 and 5 show that it is mounted for rotation within turret 50 by being positioned within a base plate 108 aperture within which is press fitted a bearing 110. Bearing 110, in turn, is covered by an annular dust shield 112 having a central aperture which surmounts the viewing tube 22 when the turret 50 is operationally oriented for carrying out the cross-cylinder test. Use of a bearing as at 110 is desirable for the instant application inasmuch as the small motors utilized as at 100 exhibit a relatively small torque, consequently, friction should be minimized. Additionally, the position of the ring gear 106 with respect to worm gear 100 should be precisely maintained to avoid any backlash or binding. FIG. 4 shows that cross-cylinder lens 66 is mounted within a bezel which, in turn, is coupled at the noted flip axis to a pair of shafts 114 and 115 extending to oppositely disposed knurled knobs 70. The locus of pivotal movement of the lens 66 at the apex thereof is represented by dashed line 66′ in FIG. 4. The worm gear form of drive provided to the cross-cylinder lens mount positively resists rotational moments induced by thrusts imposed thereon by the practitioner in carrying out a cross-cylinder lens "flipping" procedure. Such procedure otherwise imposes such moment into the gear train to promote backlash type inaccuracies.

In accordance with the instant invention, no gear train association is present between the axis control knob as represented at 34 in conjunction with battery 12 and corresponding rotatable lens mount 62 within turret 50. Motor 100 carries out all rotation of mount 62 operating in conjunction with worm drive 102 and worm gear 106. To synchronize the desired axial orientation of cross-cylinder lens 66 with the corresponding orientation of axial control knob 34, an absolute position encoding arrangement is provided which operates in conjunction with both lens drive and adjustment components 62 and 34. Structured substantially identically, the encoding assembly for control knob 34 is shown in FIG. 3 in general at 120, while the corresponding encoding assembly utilized in conjunction with lens mount 62 is shown in FIGS. 3 and 5 at 122.

FIG. 5 reveals that the encoding assembly 122 is formed comprising an annulus or disk shaped code carrier 124 which is mounted upon the inwardly disposed cylindrical region 126 of lens mount 62. Code carrier 124 is fixed in position by oppositely disposed retainer rings 128 and 130 slidably positioned over and retained upon cylindrical portion 126.

The positional code carried by code carrier 124 is read optically through the utilization of a light source which may be provided, for example, as an IR region LED shown at 135 in FIG. 5. Light is piped or directed from source 135 via a light guide 134 which may be present, for example, as a light transmissive acrylic rod. Other light guidance arrangements will occur to those skilled in the art. Rod 134 is mounted within the upstanding portion an encoder mount 136 which, additionally, supports a mask 138. Mask 138 is configured having an elongate slit to confine the light from light guide 134 to a narrow elongate region positioned immediately above code carrier 124. Positioned on the opposite side of code carrier 124 is a linear array 140 of discrete photo detectors which may be configured as phototransistors. These phototransistors are bonded to a ceramic substrate 142 which, in turn, is attached to a base region 144 of mount 136. The encoder mount is retained upon base plate 108 by machine screws as at 150 and 151.

To achieve a desired positioning and readout accuracy for the cross-cylinder lens, the code provided at carrier 140 is of an 8-bit, selectively opaque-transparent variety and optical position information is detected by the corresponding eight photodetectors at array 140. Looking additionally to FIG. 6, the substrate 142 is shown in enlarged detail as supporting eight discrete photodiodes which may be provided, for example as type OPC600L silicon phototransistors marketed, for example, by Optron, Inc. of Carrollton, Tex. Fabricable in very small dimension, for example, havng an active region of about 0.018 inches square, the phototransistors are mounted having common collectors attached to a conductive layer 146 and the emitters of each are coupled by gold wires to discrete gold leads within an array thereof represented generally at 148. With the array, a unique 8-bit position signal is generated for each degree of orientation of the lens mount 62.

Figure 7:
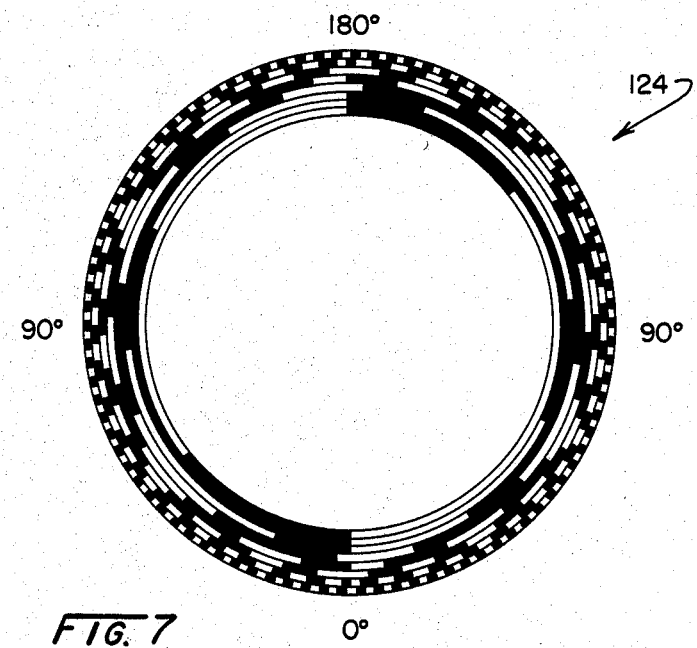
FIG. 7 is a plan view of a code carrier ring utilized with the refractor of FIG. 1.

Turning to FIG. 7, code carrier 124 is revealed as well as the position code which is formed therewith. To provide at least a 1° of accuracy readout, the disk 124 is subdivided to provide a coded readout for each one degree sector thereof. In keeping with the conventional arrangement of angular orientation identification, the entire disk is divided into two identical 180° regions. A variety of coding approaches will occur to those skilled in the art, for example, the reading of angles which extend from 0 through 180 degrees for each half of the disk requires an 8-bit binary encoding within each sector of one degree. The code is provided by selectively alternating light and dark intervals which essentially are arranged in concentric rings. By utilizing the above-described narrow light source formed of shield 138 operating in conjunction with source 135 and rod 134 narrow illumination to the 1° sectors is provided and the very narrow (within a 1° sector) array of photo detectors 140 provides the corresponding readout. A code arrangement other than binary can be contemplated for use with the code carrier 124, for example, a binary coded decimal (BCD) arrangement may be used. However, such use is with the attendant disadvantage that nine bits of information and a consequent nine concentric code rings are required which imposes an undesirable space requirement. Further considered in electing an appropriate code for the carrier 124 is the possibility for obtaining spurious readings during a transition from one degree of angle to a next adjacent one. Inasmuch as the code defining geometry and optical sensors may no t be fabricated with required tolerance, a transition of one bit may occur before that of another to result in a momentary false reading. While multiple readings may be taken to avoid this situation, another approach in avoiding such problem is the utlization of a cyclical code such as a Gray code. With such a code, a transition from one degree to position to another is evidenced by a 1-bit change. A Gray code arrangement, thus is the preferred embodiment for the instant invention. The ring encoder may be provided as a series of opaque blocks which are formed upon the transparent plastic annulus shaped carrier 124. Assigning the transparent regions to have a "0" value and corresponding opaque regions to have a "1" value, such a Gray code, for example, may be provided in accordance with the partial listing Chart 1 below, showing code values for 1° through 80°, the entire code being represented in FIG. 7.

TABLE I

| Setting Degrees | Gray Code Inside | Gray Code Outside | Setting Degrees | Gray Code Inside | Gray Code Outside | Setting Degrees | Gray Code Inside | Gray Code Outside | Setting Degrees | Gray Code Inside | Gray Code Outside |
| --- | --- | --- | --- | --- | --- | --- | --- | --- | --- | --- | --- |
| 1 | 0 0 0 0 0 0 0 1 | | 21 | 0 0 0 1 1 1 1 1 | | 41 | 0 0 1 1 1 1 0 1 | | 61 | 0 0 1 0 0 0 1 1 | |
| 2 | 0 0 0 0 0 0 1 1 | | 22 | 0 0 0 1 1 1 0 1 | | 42 | 0 0 1 1 1 1 1 1 | | 62 | 0 0 1 0 0 0 1 1 | |
| 3 | 0 0 0 0 0 0 1 0 | | 23 | 0 0 0 1 1 1 0 0 | | 43 | 0 0 1 1 1 1 1 0 | | 63 | 0 0 1 0 0 0 0 0 | |
| 4 | 0 0 0 0 0 1 1 0 | | 24 | 0 0 0 1 0 1 0 0 | | 44 | 0 0 1 1 1 0 1 0 | | 64 | 0 1 1 0 0 0 0 0 | |
| 5 | 0 0 0 0 0 1 1 1 | | 25 | 0 0 0 1 0 1 0 1 | | 45 | 0 0 1 1 1 0 1 1 | | 65 | 0 1 1 0 0 0 0 1 | |
| 6 | 0 0 0 0 0 1 0 1 | | 26 | 0 0 0 1 0 1 1 1 | | 46 | 0 0 1 1 1 0 0 1 | | 66 | 0 1 1 0 0 0 1 1 | |

TABLE I-continued

| Setting Degrees | Gray Code Inside | Gray Code Outside | Setting Degrees | Gray Code Inside | Gray Code Outside | Setting Degrees | Gray Code Inside | Gray Code Outside | Setting Degrees | Gray Code Inside | Gray Code Outside |
|---|---|---|---|---|---|---|---|---|---|---|---|
| 7 | 0 0 0 0 | 0 1 0 0 | 27 | 0 0 0 1 | 0 1 1 0 | 47 | 0 0 1 1 | 1 0 0 0 | 67 | 0 1 1 0 | 0 0 1 0 |
| 8 | 0 0 0 0 | 1 1 0 0 | 28 | 0 0 0 1 | 0 0 1 0 | 48 | 0 0 1 0 | 1 0 0 0 | 68 | 0 1 1 0 | 0 1 1 0 |
| 9 | 0 0 0 0 | 1 1 0 1 | 29 | 0 0 0 1 | 0 0 1 1 | 49 | 0 0 1 0 | 1 0 0 1 | 69 | 0 1 1 0 | 0 1 1 1 |
| 10 | 0 0 0 0 | 1 1 1 1 | 30 | 0 0 0 1 | 0 0 0 1 | 50 | 0 0 1 0 | 1 0 1 1 | 70 | 0 1 1 0 | 0 1 0 1 |
| 11 | 0 0 0 0 | 1 1 1 0 | 31 | 0 0 0 1 | 0 0 0 0 | 51 | 0 0 1 0 | 1 0 1 0 | 71 | 0 1 1 0 | 0 1 0 0 |
| 12 | 0 0 0 0 | 1 0 1 0 | 32 | 0 0 1 1 | 0 0 0 0 | 52 | 0 0 1 0 | 1 1 1 0 | 72 | 0 1 1 0 | 1 1 0 0 |
| 13 | 0 0 0 0 | 1 0 1 1 | 33 | 0 0 1 1 | 0 0 0 1 | 53 | 0 0 1 0 | 1 1 1 1 | 73 | 0 1 1 0 | 1 1 0 1 |
| 14 | 0 0 0 0 | 1 0 0 1 | 34 | 0 0 1 1 | 0 0 1 1 | 54 | 0 0 1 0 | 1 1 0 1 | 74 | 0 1 1 0 | 1 1 1 1 |
| 15 | 0 0 0 0 | 1 0 0 0 | 35 | 0 0 1 1 | 0 0 1 0 | 55 | 0 0 1 0 | 1 1 0 0 | 75 | 0 1 1 0 | 1 1 1 0 |
| 16 | 0 0 0 1 | 1 0 0 0 | 36 | 0 0 1 1 | 0 1 1 0 | 56 | 0 0 1 0 | 0 1 0 0 | 76 | 0 1 1 0 | 1 0 1 0 |
| 17 | 0 0 0 1 | 1 0 0 1 | 37 | 0 0 1 1 | 0 1 1 1 | 57 | 0 0 1 0 | 0 1 0 1 | 77 | 0 1 1 0 | 1 0 1 1 |
| 18 | 0 0 0 1 | 1 0 1 1 | 38 | 0 0 1 1 | 0 1 0 1 | 58 | 0 0 1 0 | 0 1 1 1 | 78 | 0 1 1 0 | 1 0 0 1 |
| 19 | 0 0 0 1 | 1 0 1 0 | 39 | 0 0 1 1 | 0 1 0 0 | 59 | 0 0 1 0 | 0 1 1 0 | 79 | 0 1 1 0 | 1 0 0 1 |
| 20 | 0 0 0 1 | 1 1 1 0 | 40 | 0 0 1 1 | 1 1 0 0 | 60 | 0 0 1 0 | 0 0 1 0 | 80 | 0 1 1 1 | 1 0 0 0 |

Figure 8:
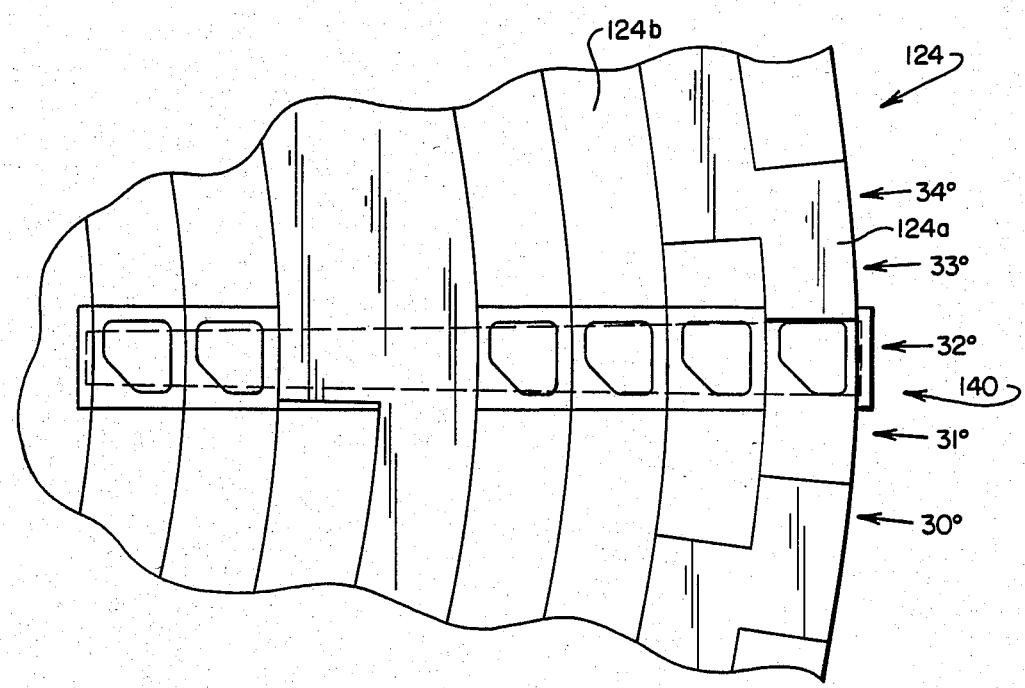
FIG. 8 is an enlarged sectional view of one portion of the code carrier ring shown in FIG. 7.

Referring to FIG. 7, a Gray code as partially set forth in Table I above is shown implemented in a ring or disk-shaped carrier 124. In keeping with a modulo 180° approach as provided in earlier refractors, carrier 124 is formed having two identical code regions, each ranging from 0° to 180°. Within each code region, the outer ring may be seen to be a uniform alternation between transparent and opaque block shapes. Each of these block shapes constitutes two degrees. Thus, for each transition from one degree to another, one-half of such block distance is traversed. Looking to FIG. 8, a fragmentary and highly enlarged sector of the code carrier shown in FIG. 7 is revealed. Beneath this sector there is shown in correspondingly enlarged scale the array of phototransistors 140. The opaque portions of the code in FIG. 8 are shown in shaded fashion as at 124a, while transparent regions are represented at 124b. With the orientation shown in FIG. 8, the array 140 will read out an 8-bit Gray code representation for the value 32°. Note that a transition from a Gray code reading of 32° to 33° will involve a change only in one ring of the code carrier, here the outside one. This avoids the ambiguity which otherwise may be encountered with multiple code transitions to define a given annular change. Such Gray code values then will be seen to be converted to a binary number signal which, in turn, is converted to a binary coded decimal signal for use in driving the axis reading display, for example, at 42 in FIG. 1.

Figures 6, 9:
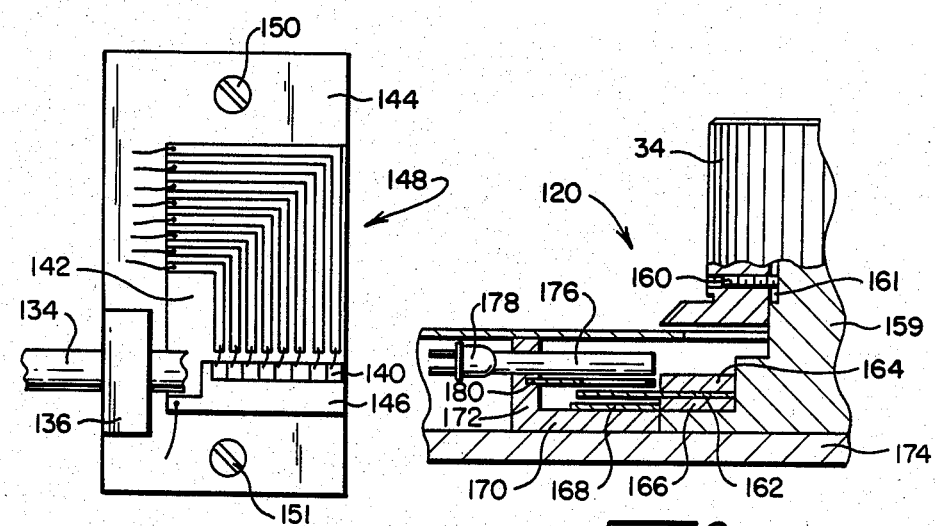
FIG. 6 is a plan view of an encoding structure used with the instant invention.
FIG. 9 is a fragmentary sectional view taken through the plane 9—9 shown in FIG. 3.

A substantially identical encoding assembly is provided at 120 in conjunction with the axis control knob 34. Turning to FIG. 9, an enlarged cross-sectional representation of such assembly is revealed. Axis control knob 34 serves to align the cylinder axes of the disk mounted cylinder lenses within battery 12. As the practitioner rotates knob 34, the axis gear shaft 159, which is fixed to knob 34 by two set screws, one of which is shown at 160, extending into a groove 161, is correspondingly rotated to provide a gear drive to the cylinder axis setting mechanism of battery 12. This rotative movement is "tracked" by encoding assembly 120 by virtue of the mounting of a code carrier 162 to axis gear shaft 159. Mounting is provided through the utilization of two rings 164 and 166 which are press fitted over the shaft 159. Code carrier 162 carries an identical code as described at 124 in conjunction with FIG. 7. As before, the code carrier 162 operates in conjunction with an array of eight photoconductors represented at 168 which are supported upon the base region 170 of an encoder mount 172. Mount 172 is connected through its base region 168 to a base plate 174 of battery 12. As before, the encoder mount 172 supports a light transmissive cylindrical acrylic light guide 176 in a position arranged to receive IR region illumination from a light emitting diode 178. To concentrate the illumination emanating from guide 176 along a narrow region extending above a 1° sector of the code formed upon carrier 162, a slit containing mask is provided as representated at 180. With the arrangement thus shown, any manipulation amounting to about 1° of movement of knob 34 will be detected by encoding assembly 120 which, in turn, will derive an 8-bit Gray code position signal.

During the performance of a Jackson cross-cylinder test, any manipulation by the practitioner of knob 34 is essentially, immediately responded to by movement of the lens mount 62 of the cross-cylinder assembly. In this regard, the motor 100 is selected having an output rotational speed of about 4,000 rpm which is utilized in conjunction with about a 60 to 1 reduction in conjunction with worm drive 102. Thus, about one-half second is required to rotate the lens mount 62 through 180°. This is essentially as fast as knob 34 can be practically rotated by the practitioner through such a degree range. As noted above, the same arrangement is provided for the components of battery 14.

The form of encoding developed in conjunction with encoding assemblies as at 120 and 122 is absolute in nature in that the system will always be responsive to the instantaneous position of both the cross-cylinder lens and an associated axis control knob. This approach not only achieves very high accuracies, for example the motor is capable of stopping within about one-eighth of a degree, but also accommodates automatically for any mechanical wear which may be evidenced in lens mountings, positional gears or the like. The absolute encoding approach inherently eliminates calibration requirements otherwise occasioned by wear. As is apparent, the preferred optical encoding approach also itself exhibits no wear over essentially a lifetime of utilization of the instrument. Through the utilization of a microprocessor control, the instant instrumentation arrangement also may be made "user friendly" in that by the utilization of an absolute encoding approach, no initialization procedures are required of the practitioner to commence an examination. For example, through the alternative utilization of stepper drives and the like, some arrangement must be made to return all settings to 0 or an initial position in order to carry out appropriate position defining counting and the like.

Figure 10:
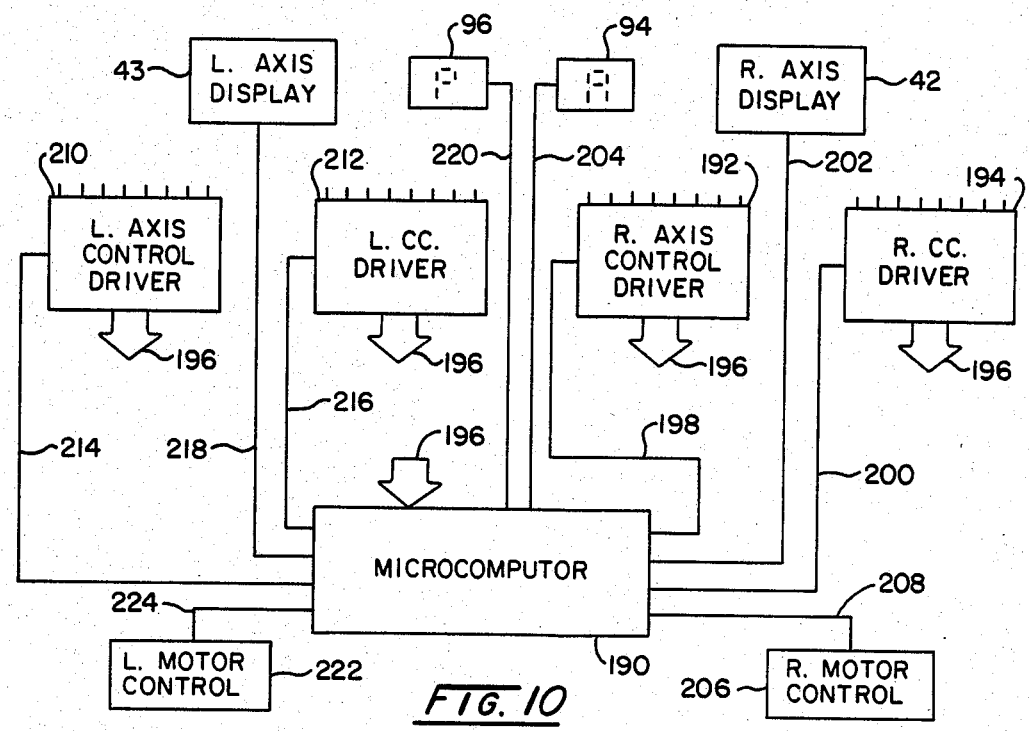
FIG. 10 is a block schematic representation of a circuit used with the refractor of FIG. 1.

Turning to FIG. 10, a block diagrammatic representation of the circuit control of the invention is presented. The control arrangement of the invention is microcomputer based, for example utilizing a type 8035 microcomputer marketed by Intel Corporation, Santa Clara, Calif. This microcomputer is represented by block 190 which is additionally assumed to include a program memory function. The microcomputer function 190 scans the setting outputs of batteries 12 and 14 in an alternating sequence and provides appropriate updating and the like in response to practitioner manipulation of the control axis knobs 34 or 36 as well as alterations of the orientations of switches 90 or 92. In this regard, the practitioner need not actuate any switch or the like to operate either of the batteries 12 or 14. In the description of FIG. 10, circuit components operating in conjunction with battery 12 initially are described in the interest of clarity. However, in a later discussion of the control instructions of the microcomputer represented at block 190 a control sequence commencing with the components of battery 14 is set foth. It should be understood that such sequence may commence in conjunction with either battery.

The 8-bit position code data which, for example, is developed from encoding assemblies 120 and 122 and which represents a Gray code output is coupled to the eight inputs of respective right axis control driver 192 and right cross-cylinder driver 194. These octal line drivers are provided inasmuch as the signals which are developed by the phototransistor arrays of the assemblies 120 and 122 exhibit very small current levels, for example in the order of microamperes. Drivers 192 and 194 serve to evolve eight-bit outputs evidencing appropriately enhanced current characreistics in correspondence with the inputs thereto. The enhanced outputs then are directed to a common bus system represented throughout FIG. 10 at 196 which is directed to the appropriate I/O ports of microcomputer function 190. Because of the common bus connections, enablement is required for drivers 192 and 194 as represented by enabling input lines directed thereto, respectively, along lines 198 and 200 from microcomputer 190. The microcomputer function 190 evaluates the right axis control knob orientation, converts the Gray code data to binary format and, in turn, converts the resultant binary format to binary coded decimal form to effect a display of the axis orientation at display 42. This association with the display is represented by line 202 extending to the correspondingly identified block 42. The microcomputer 190 additionally evaluates the orientation of mode switch 90 as it effects the readout at mode display 94 as represented by a line 204, and with the elected mode information, carries out a comparison between the axial orientation information developed from drivers 192 and 194, such evaluation taking place following a conversion of these values to binary form. In the event an axis mode is present, then the value of the axis orientation developed from driver 192 is adjusted by an amount equivalent to 45° and a comparison between that adjusted value and the value of the output from driver 194 is made. Where these values are not equal, then a right battery motor control represented at block 206 is energized in an appropriate directional sense, the association effecting such control being represented schematically by line 208. This control input is maintained until such time as the microcomputer observes that the angular position of the control knob and cross-cylinder lens are identical. The motor is then stopped. The mode display as represented by repeated numeration 94 in FIG. 10 will be seen to be provided by the simple expedient of direct connection of one segment of the seven segment display with switch 90.

The left eye battery 14 of the instrument 10 is controlled in identical fashion, the outputs of the optical encoders thereof being directed to a left axis control driver circuit represented by block 210 and the 8-bit Gray code outputs of the cross-cylinder encoding assembly being directed to the input of a driver circuit represented at block 212. These drivers are selectively enabled by microcomputer function 190 as represented by respective lines 214 and 216 extending thereto. As before, the microcomputer function 190 responds to the left axis control driver output at bus 196 to convert the Gray code data available therefrom to binary and then to binary coded decimal format for purposes of effecting a display of the control knob 36 axis orientation at display 43, now represented in FIG. 10 by a block. The control to display 43 is represented schematically by line 218. Microcomputer function 190 also responds to the orientation of mode switch 92 as represented by line 220 extending to the display function represented as a block 96. As before, a comparison of the outputs of drivers 210 and 212 as affected by the particular power or axis mode information is made and, where appropriate, a drive input is directed to the motor effecting the drive of lens mount 64. Appropriate directional motor drive signals are provided through a motor control circuit represented by block 222 under the control of microcomputer function 190, such control association being represented schematically by line 224. The above cycle between batteries 12 and 14 is continuous as long as the control circuit is activated. Generally, the control circuit represented by FIG. 10 is incorporated in the opthalmic instrument stand associated with refractor 10.

Figure 11A:
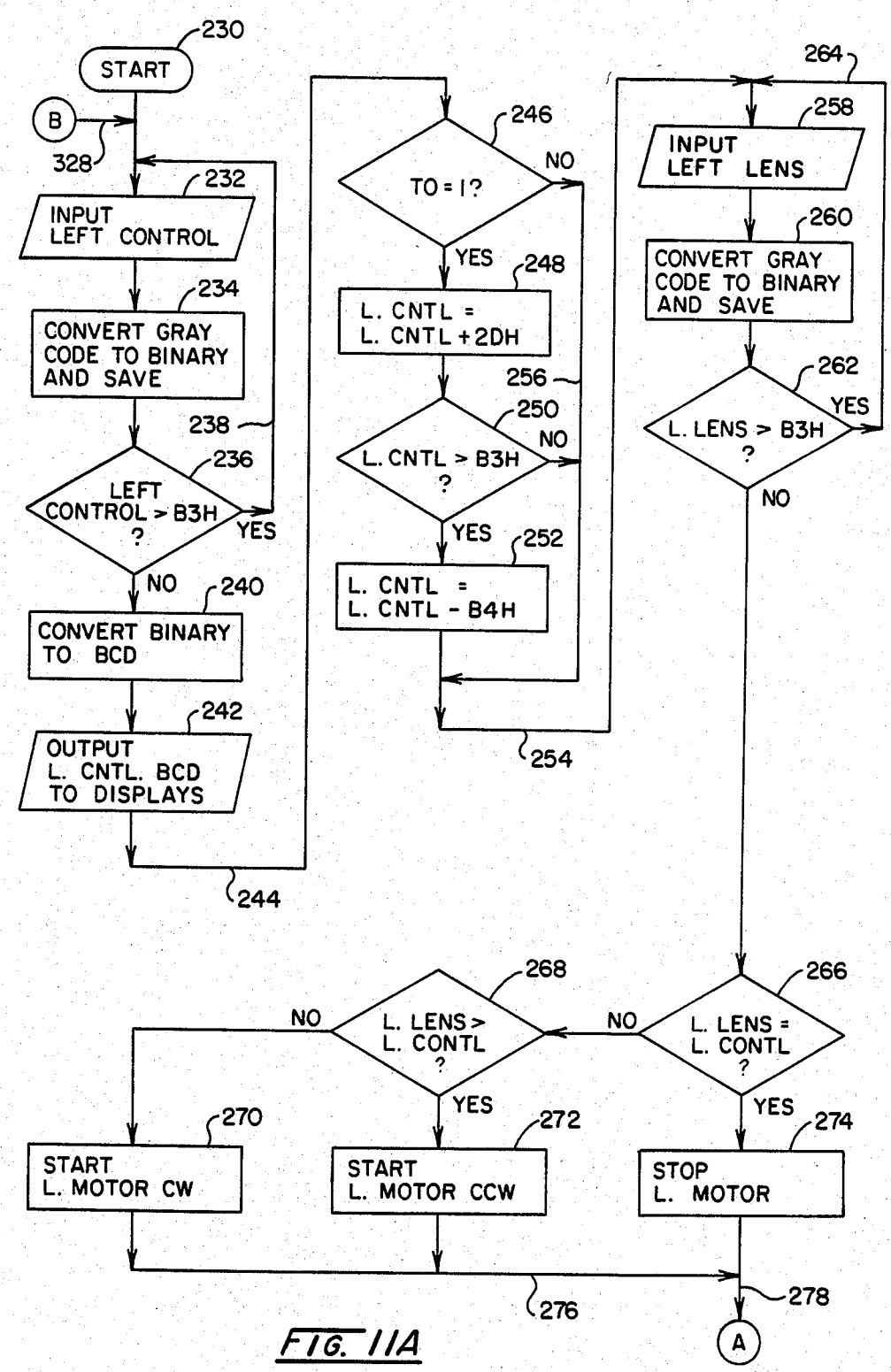
FIGS. 11A and 11B are a flow diagram of the microprocessor instructions utilized with the circuit of the refractor of FIG. 1.
Figure 11B:
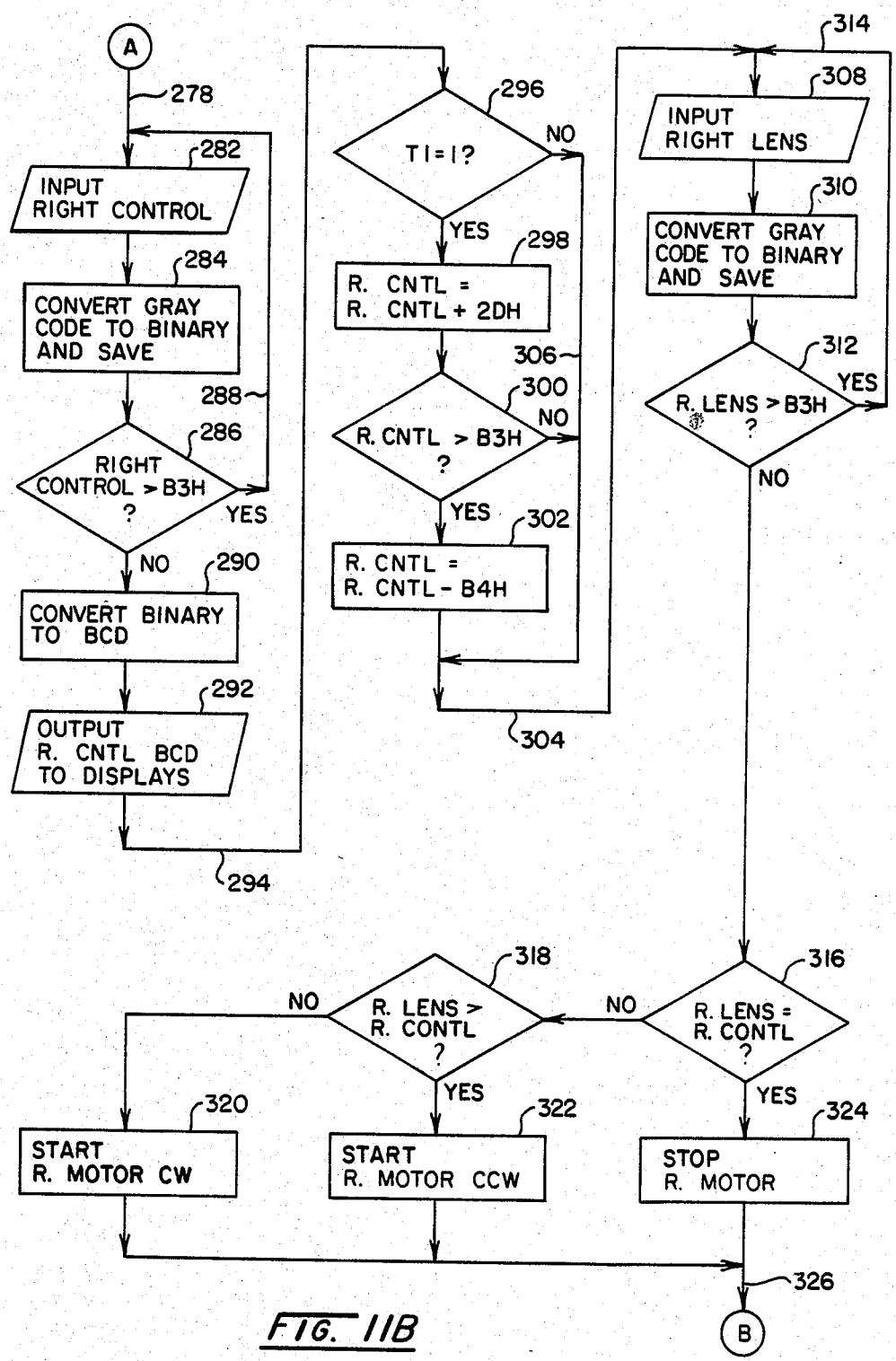

Referring to FIGS. 11A and 11B, a flow diagram is provided describing the control program under which the microcomputer function represented at block 190 performs. Referring to FIG. 11A, the program is commenced with initialization procedures and the like as represented at start terminal 230. Upon such start, the program acquires the Gray code data from the encoding assembly associated with axis control knob 36. The inputting of these data is represented at block 232. Upon acquiring such data, they are converted to binary format and retained as represented at block 234. Using these retained data, as represented at block 236, an inquiry is carried out to determine whether the value of angular orientation of control knob 36 is greater than 179°, herein represented in hexadecimal form as "B3". In the event of an affirmative response, the data are in error and, as represented by loop line 238, the program returns to the input at block 232 to repeat the recovery of data.

In the event the inquiry represented at block 236 derives a negative response, then as represented at block 240, the angular orientation information from the control knob 36 is converted from binary form to binary coded decimal (BCD) format as represented at block 240. Upon effecting such conversion, as represented at block 242, the BCD data are outputted to the left eye position display represented in FIG. 1 at 43. The program then continues, as represented by line 244, to carry out the inquiry represented at block 246 determining the orientation of mode switch 92. A logic high level developed with the switch (T1=1) indicates the practitioner's election of an axis mode of operation and, accordingly, an affirmative response directs the program to the instruction at block 248 wherein the value for the axial orientation of left control knob 36 is incremented by the value 45° represented in hexadecimal fashion as "2D". Upon incrementing the axis control knob value, as represented at block 250, an inquiry is made as to whether the resultant value is greater than 179° as represented in the block in hexadecimal form. In the event that the value is greater than 179°, then as represented at block 252, the value 180° herein represented in hexadecimal fashion as "B4", is subtracted from the total value and the program progresses as represented at line 254. Returning to block 246, where the inquiry thereat indicates a high logic level is not being monitored at switch 92, then the program diverts immediately to line 254 as represented by line 256. This diversion provides for power mode lens adjustment. Similarly, where the inquiry at block 250 indicates that the adjusted left control value is not greater than 179°, the program diverts to line 254, again as represented at line 256.

Line 254 leads to block 258 wherein instructions are provided for inputting of data representing the angular orientation of the left eye position cross-cylinder lens within mount 64. Upon inputting these data as presented in Gray code format, the Gray code format is converted to binary form as represented at block 260 and is retained following which, as represented at block 262, a determination is made as to whether the retained value is greater than 179°, again represented in hexadecimal form as "B3". In the event of an affirmative response, as represented at line 264 the program returns to again look to the input at block 258, in realization of an input error. Where the inquiry at block 262 is in the negative, the program progresses to the inquiry represented at block 266 wherein a determination is made as to whether the value of the angular orientation of the left eye cross-cylinder lens is equal to the axial orientation of the left axis control knob 36. Where these values are not equal, as represented at block 268, a determination is made as to whether the binary value for the orientation of the left cross-cylinder lens is greater than the binary value for the axial orientation of axis control knob 36. Where the inquiry results in a negative answer, as represented at block 270, the motor control circuit is activated to energize the lens drive motor associated with lens mount 64 in a clockwise direction. Where the inquiry at block 268 results in a determination that the lens position value is greater than the axis orientation value corresponding with control knob 36, then as represented at block 272 the motor drive circuit commences the energization of the lens mount drive motor in a counter-clockwise sense. When the inquiry at block 266 indicates that the values for the setting of control knob 36 as appropriately adjusted and the value for the setting of the cross-cylinder lens are equal, then as represented at block 274 the left lens drive motor is stopped. Following the instructions represented at blocks 270, 272 and 274, as represented by lines 276 and the terminal labeled "A", the program commences to carry out the same sequence of instructions and the like with respect to the right eye battery 12. It may be observed from the above, that for a power mode setting of switch 92, no incrementation is made to the value for axis orientation of knob 36 and the cross-cylinder lens 68 will be oriented such that its minus axis is aligned with the axis of the cylinder lens positioned before the viewing tube.

The terminal labeled "A" is seen to continue in FIG. 11B with the flow diagram setting forth instructions in substantially the same fashion as those described in conjunction with FIG. 11A. Accordingly, the program starts with the same terminal designation, "A" which leads to block 282 indicating that the Gray code data corresponding with the setting of axis control knob 34 is recepted. Following such reception, as represented at block 284 the data are converted to binary format and as represented at block 286, a determination is made as to whether the value is greater than 179°. If that is the case, then as represented at loop line 288, erroneous data are at hand and the input procedure is repeated. In the event of a negative response to the inquiry at block 286, then as represented at block 290, the binary value of the axis setting is converted to binary coded decimal format (BCD) and as represented at block 292, this informations in BCD format is outputted to the right eye battery 12 display 42. The program then continues as shown at line 294 to the inquiry at block 296 wherein a determination is made as to whether the mode control switch 190 is in an axis or power mode. Where it is in an axis mode, a logic high is detected to provide an affirmative response whereupon a 45° adjustment in the orientation of the cross-cylinder lens mount 62 is carried out. Accordingly, as represented at block 298, the numeric value for the right axis control knob setting 34 is adjusted by incrementing it 45°. The program then progresses to the inquiry at block 300 wherein a determination is made as to whether the adjusted value derived at block 298 is greater than 179°. Where that is the case, then as represented at block 302, the read value 180° then is subtracted from the adjusted value. The program then proceeds to scan the cylinder lens setting as represented at line 304. Returning to block 296, where mode switch 90 is in a power mode setting, then the microcomputer will witness a low logic level at its port T1 and, as represented by line 306, a power mode operation is carried out without a 45° incrementation and the program diverts to line 304. Similarly, where the inquiry at block 300 is in the negative, the resultant numeric signal is appropriate for modulo 179° performance and the program diverts as represented at line 306 to line 304.

The program then looks to the Gray code input from the encoder assembly 122 associated with lens mount 62 as represented at block 308. As before, the inputted Gray code value is converted to binary form as represented at block 310 and the program inquires as to whether the value so obtained is greater than 179° as represented at block 312. In the event that is the case, then as represented by loop line 314, an error is at hand and the right eye position cross-cylinder lens orientation is re-examined. A negative response at block 312 leads to the inquiry at block 316 at which position the inquiry is made as to whether the axis setting value for the right eye position cross-cylinder lens at lens mount 62 is equal to the corresponding axis setting of axis control knob 34. In the event that it is not, then as represented at block 318 a determination is made as to whether the setting corresponding with the cross-cylinder lens within mount 62 is greater than the setting of the axis control knob 34. In the event that it is not, then as represented at block 320, motor 100 is energized to cause a clockwise rotation of lens mount 62. In the event the inquiry at block 318 is in the affirmative, then as represented at block 322, motor 100 is energized to effect a counter-clockwise rotation of lens mount 62.

Where the inquiry at block 316 indicates that the settings of axis control knob 34 and lens mount 62 are equal, then as represented at block 324, the motor 100 is de-energized. The program then proceeds as represented at line 326 to terminal "B" which re-enters the program in FIG. 11A as represented by the same terminal designation and line 328. The entire cycle accommodating both batteries 12 and 14 may be arranged to occur on a sufficiently repetitive basis such that no switching is required by the practitioner to elect one battery or the other. For example, a rate of about 100 cycles per second is found to be entirely adequate. Further, as indicated above, the cycling program may commence with either battery 12 or 14 with no effect on the performance of the instrument 10.

Figure 13:
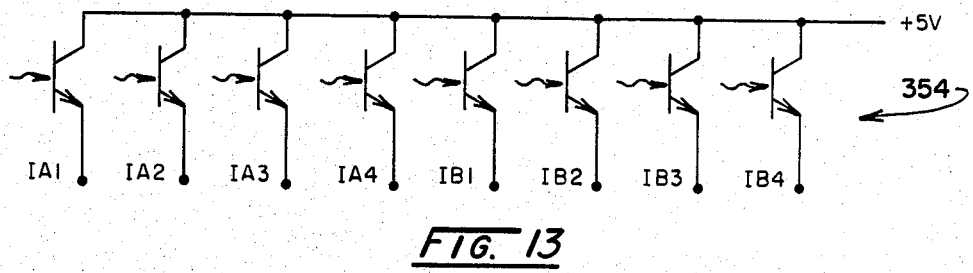
FIG. 13 is a circuit diagram of a phototransistor array utilized with the optical encoder of the instant invention.
Figure 12A:
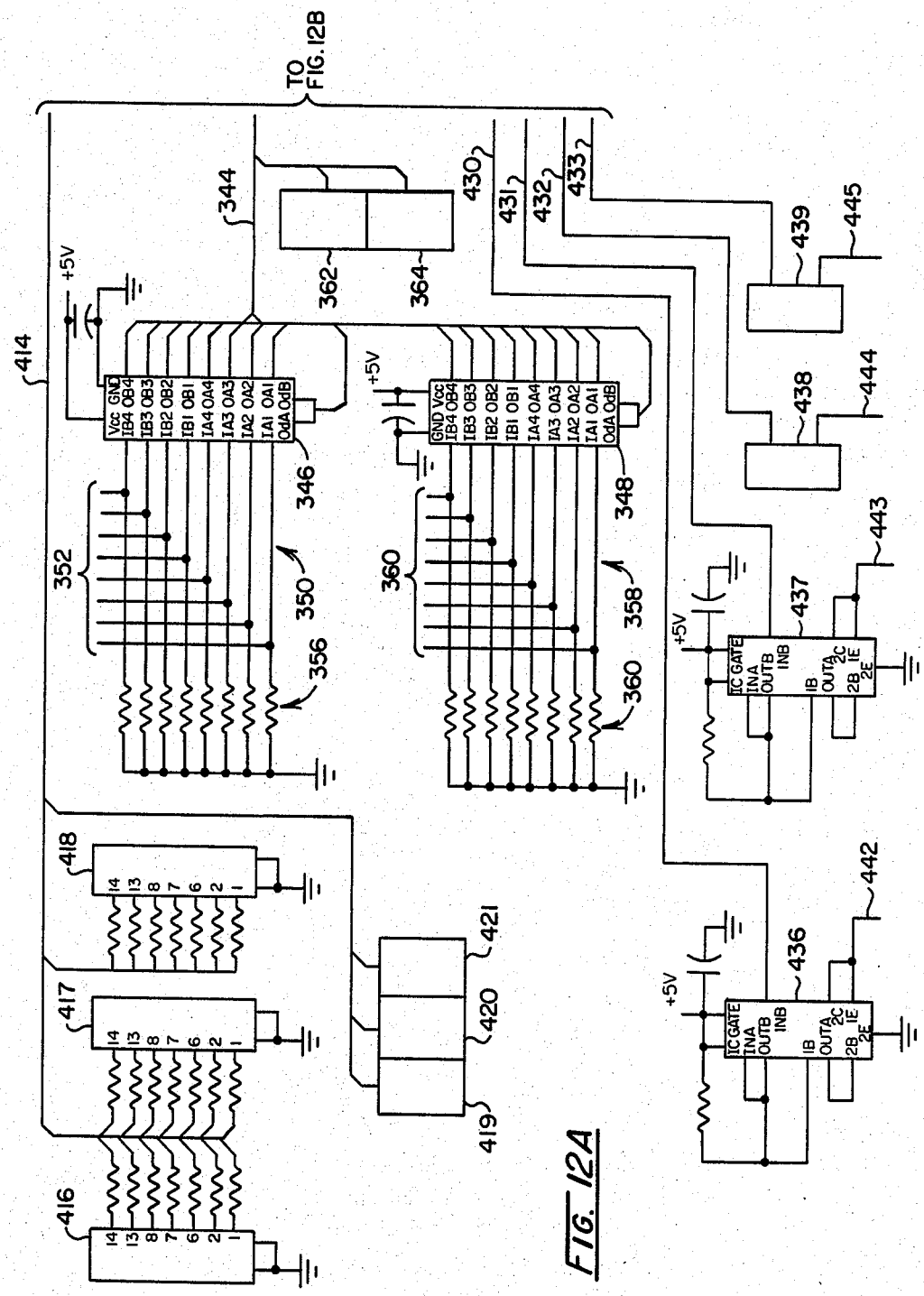
FIG. 12A and 12B are a circuit diagram of the control circuit utilized in conjunction with the refractor of FIG. 1.
Figure 12B:
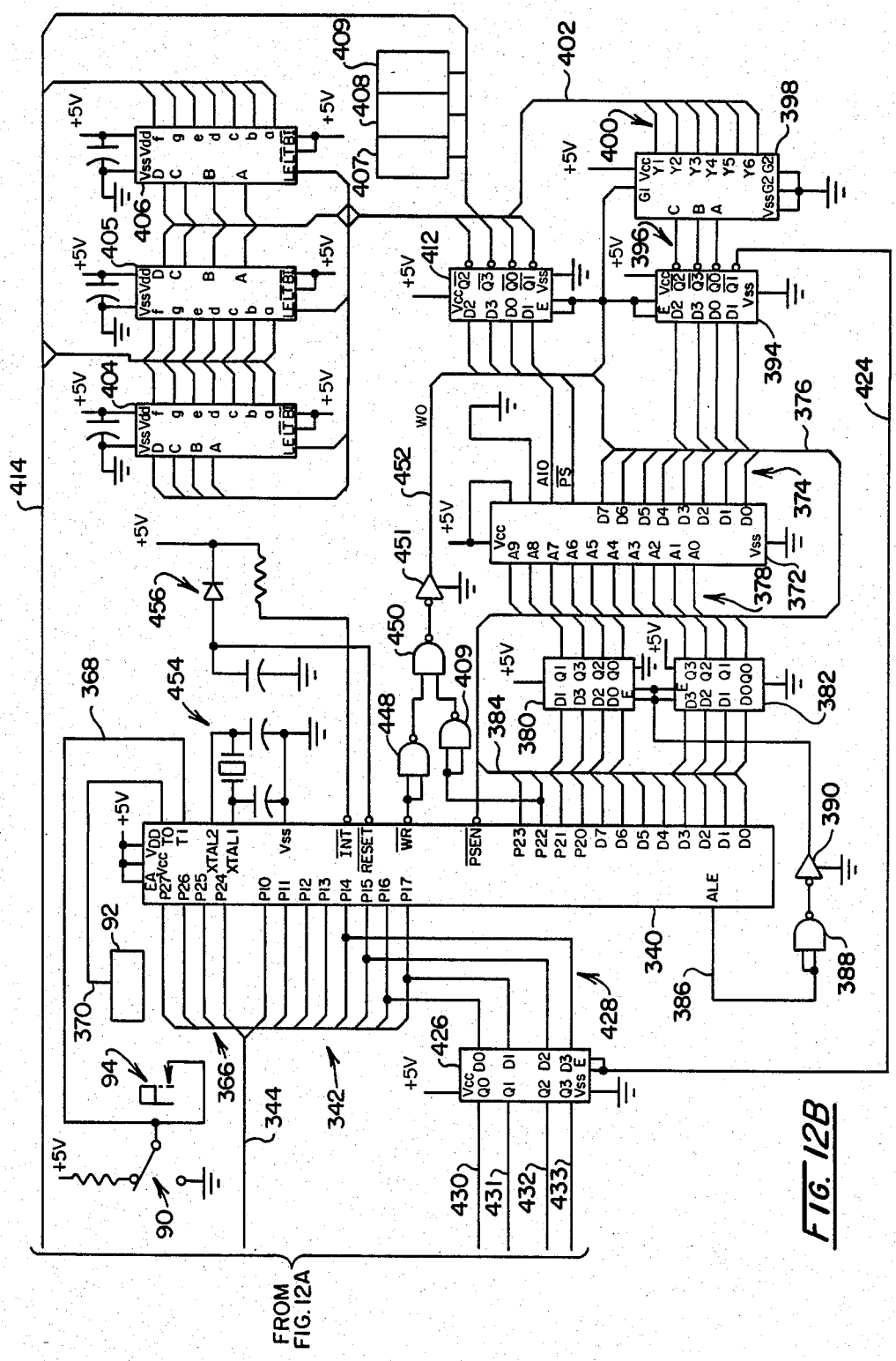

A detailed representation of the circuit implementing the above program and corresponding with the generalized discussion associated with FIG. 10 is revealed in conjunction with FIGS. 12A, 12B and 13. FIG. 12B should be considered as positioned to the right of FIG. 12A in the discourse to follow. Looking to FIG. 12B, the microcomputer control of the circuit is represented at 340 and, as earlier described, may be of a type 8035 marketed by Intel Corporation (supra). Ports P10 through P17 of the microcomputer 340 are coupled in a common bus arrangement commencing with a lead array 342 extending from bus 344 to the earlier-described octal line drivers associated with each of the encoder assembly 8-bit Gray code outputs. For example, bus 344 is seen to extend to the OA1-OA4 and OB1-OB4 outputs of two type MM74C240 inverting octal line drivers 346 and 348. These drivers are marketed, for example, by National Semi-Conductor Corporation, Santa Clara, Calif. As indicated above, these drivers serve to enhance the very low current level signal derived from the phototransistor arrays associated with each of the optical encoder assemblies of instrument 10. In this regard, the output terminals IA-1-IA4 and IB1-IB4 are coupled through line arrays 350 and 352 to the outputs of the left axis control knob encoder as is asscociated with knob 36 of battery 14 (FIG. 1). This coupling of the line array 352 is to the emitter electrodes of the phototransistor array. Looking momentarily to FIG. 13, a typical circuit representation of such an array is represented at 354. Note, that the collectors of each of the phototransistors are coupled to +5 v supply, while the emitters thereof are coupled terminals, IA1-IA4 and IB1-IB4 of driver 346 through line array 350 (FIG. 11A). This terminal identification holds for all of the octal drivers of the circuitry. Note that in the arrangement shown in FIG. 12A, phototransistor sensitivity, setting resistors as at 356 are coupled within the lines of array 350 to ground.

In similar fashion, octal line driver 348 is coupled to bus 344 in identical fashion such that its output terminals are in connection with the terminals P10–P17 of microcomputer 340. The input to driver 348 is coupled through line array 358 and 360 to the Gray code output of the encoder assembly associated with rotatable lens mount 60 for the left eye position of battery 14. As before, the connections of line array 360 with this encoder are derived from the phototransistor emitter terminals as described in connection with FIG. 13. Additionally, as before, the line array 358 is coupled through phototransistor sensitivity setting resistor array 360 to ground. An identical arrangement is provided for the right eye battery 12 and, in the interest of clarity, the octal line decoder associated with right eye battery 12 control axis as at 120 is shown at block 362, while the corresponding octal driver associated with encoder assembly 122 is represented at block 364. Drivers 364, 362, 348 and 346 respectively are enabled from corresponding ports P24-P27 of microcomputer 340. Note, that the latter ports are coupled to bus 344 through line array 366.

As indicated earlier herein, microcomputer 340 responds to the orientation of mode switches 90 and 92 to determine whether the practitioner has elected to carry out cross-cylinder testing in an axis or a power mode. Where an axis mode is provided, then microcomputer 340 responds to a logic high to carry out a 45° adjustment of axis control knob readout. FIG. 12B shows the details for operating switch 90 as well as for energizing the corresponding mode display 94. Note that switch 90 switches between ground or logic low and +5 v supply. The switch is coupled with line 368 which is coupled to the T1 terminal of microcomputer 340. Display 94 is represented in FIG. 12B as a 7-segment LED display, the selective illumination of only one segment of which provides for the display of an "A". When switch 90 is converted to provide a logic low condition, then the noted segment of display 94 is not energized to provide a "P" display readout. Through the use of an LED readout, the practitioner may perceive the mode display in a darkened room. In similar fashion, switch 92 is represented by a similarly numbered block communicating via line 370 to terminal T0 of microcomputer 340. Accordingly, when the program of the microcomputer cycles through a control over the left eye battery, an identical type mode readout takes place as described in conjunction with block 246 in FIG. 11A.

The control instructions for the operation of microcomputer 340 is described above in conjunction with FIGS. 11A and 11B are retained in read only memory which is represented in FIG. 12B at 372. The memory 372 may, for example, be provided as a 16K(2K×8)UV erasable PROM marketed as a type 2716 by Intel, Inc. The data output terminals D0-D7 of memory 372 are coupled through lead array 374 to bus 376. Correspondingly, the address terminals A0-A9 of the memory are coupled through lead array 378 and bus 376 to a latching function comprised of two 4-bit bistable latches 380 and 382. Such latches are used as temporary storage for binary information between processing functions and I/O components. Information present as data at the D0-D3 terminals of the latches is transferred to the corresponding Q outputs, Q0-Q1 when the enable, E terminal receives a logic high input. Accordingly, the data input terminals of latches 380 and 382 are coupled and selectively assigned to the data terminals D0-D7 of microcomputer 340. Enablement of these latches 382 and 380 emanates from the address latch enable port (ALE) of microcomputer 340 which extends via line 386 to input NAND gate 388 and inverter buffer 390 to the enable (E) gates of the latches. Memory 372 is selectively read by microcomputer 340 by an appropriate $\overline{PS}$ signal derived from the program store enable ($\overline{PSEN}$) terminal thereof. In addition to the control instructions as described in conjunction with FIGS. 11A and 11B, the memory 372 also includes table look-up data for carrying out a conversion of the Gray code outputs of the optical encoder assemblies to binary format. An exemplary portion of such a look-up table is provided below as Table II.

TABLE II

| Gray | | | | | | | | | | | | | | | | |
|------|----|----|----|----|----|----|----|----|----|----|----|----|----|----|----|----|
| 0000 | 00 | 01 | 03 | 02 | 07 | 06 | 04 | 05 | 0F | 0E | 0C | 0D | 08 | 09 | 0B | 0A |
| 0010 | 1F | 1E | 1C | 1D | 18 | 19 | 1B | 1A | 10 | 11 | 13 | 12 | 17 | 16 | 14 | 15 |
| 0020 | 3F | 3E | 3C | 3D | 38 | 39 | 3B | 3A | 30 | 31 | 33 | 32 | 37 | 36 | 34 | 35 |
| 0030 | 20 | 21 | 23 | 22 | 27 | 26 | 24 | 25 | 2F | 2E | 2C | 2D | 28 | 29 | 2B | 2A |
| 0040 | 7F | 7E | 7C | 7D | 78 | 79 | 7B | 7A | 70 | 71 | 73 | 72 | 77 | 76 | 74 | 75 |
| 0050 | 60 | 61 | 63 | 62 | 67 | 66 | 64 | 65 | 6F | 6E | 6C | 6D | 68 | 69 | 6B | 6A |
| 0060 | 40 | 41 | 43 | 42 | 47 | 46 | 44 | 45 | 4F | 4E | 4C | 4D | 48 | 49 | 4B | 4A |
| 0070 | 5F | 5E | 5C | 5D | 58 | 59 | 5B | 5A | 50 | 51 | 53 | 52 | 57 | 56 | 54 | 55 |
| 0080 | FF | FE | FC | FD | F8 | F9 | FB | FA | F0 | F1 | F3 | F2 | F7 | F6 | F4 | F5 |
| 0090 | E0 | E1 | E3 | E2 | E7 | E6 | E4 | E5 | EF | EE | EC | ED | E8 | E9 | EB | EA |
| 00A0 | C0 | C1 | C3 | C2 | C7 | C6 | C4 | C5 | CF | CE | CC | CD | C8 | C9 | CB | CA |
| 00B0 | DF | DE | DC | DD | D8 | D9 | DB | DA | D0 | D1 | D3 | D2 | D7 | D6 | D4 | D5 |
| 00C0 | 80 | 81 | 83 | 82 | 87 | 86 | 84 | 85 | 8F | 8E | 8C | 8D | 88 | 89 | 8B | 8A |
| 00D0 | 9F | 9E | 9C | 9D | 98 | 99 | 9B | 9A | 90 | 91 | 93 | 92 | 97 | 96 | 94 | 95 |
| 00E0 | BF | BE | BC | BD | B8 | B9 | BB | BA | B0 | B1 | B3 | B2 | B7 | B6 | B4 | B5 |
| 00F0 | A0 | A1 | A3 | A2 | A7 | A6 | A4 | A5 | AF | AE | AC | AD | A8 | A9 | AB | AA |

179 Degrees = EA Gray = B3 HEX

While an algorithmic approach may be utilized for carrying out the conversion of Gray code to binary format, the above look-up technique is preferred for the instant invention.

The data terminals of microcomputer 340 additionally are coupled by bus 376 to the input terminals of a 4-bit bi-stable latch 394 which, as before, may be a type 7475. Latch 396 provides a 3-line output at array 396 which is coupled with the A-C input terminals of a one-of-eight decoder 398. Decoder 398, operating in conjunction with the 3-line input from latch 394 may be provided as a type 74LS 138 decoder which provides six discrete chip enable signals at its output terminals which are coupled through lead array 400 to bus branch 402. The chip enable signals provided through bus 402 are directed to discrete select ones of the enablement terminals (LE) of six BCD-to-7-segment decoder drivers, three of which are shown in enhanced detail at 404–406 and three of which are shown in schematic block fashion at 407–409. Decoder drivers 404–409 may be provided, for example, as type CD4511 marketed by National Semi-Conductor Corporation (supra). The 4-bit binary coded decimal signal developed by microcomputer 340 for effecting a digital output at displays 42 and 43 is submitted to the inputs of another 4-bit bistable latch 412, the outputs of which are directed to the corresponding A-D input to decoder drivers 404–409. With the arrangement thus shown, decoder drivers 404–406 are selectively enabled from decoder 398 for the purpose of providing digital input data to display 43 of left eye battery 14. Such data are directed from the decoder/drivers 404–406 along bus branch 414 to the seven inputs of 7-segment LED displays 416–418 (FIG. 12A). These digit defining LED devices 417–418 are incorporated within the left eye battery 14 display 43. In similar fashion, decoder drivers 407–409 when appropriately selected, provide a 3-digit information through bus branch 414 to 7-segment LED displays 419–421 are positioned to provide display 42 for right eye battery 12 (FIG. 1). Displays 416–421 may be provided, for example, as type MAN74A. The use of LED display readouts for axis angle value permits ease in perception by the practitioner in the normally encountered dark room environment of ophthalmic testing.

Returning to FIG. 12B, the $\overline{Q1}$ terminal of latch 394 serves to provide a chip enablement signal along line 424 to the enable, E, input terminal of a motor drive latch 426. Latch 426 may be provided as a type 74LS75, having its D0–D3 input terminals coupled with microcomputer 340 through line array 428 and its Q0–Q3 output coupled through respective lines 430–433 to four motor drive circuits 436–439. Provided, for example, as type DS75450 Series Dual Peripheral Drivers marketed by National Semi-Conductor Corporation, two of the drivers, 436 and 437 are shown in detail. (See FIG. 12A) In the interest of clarity, circuits 438 and 439 are shown in block schematic fashion.

Line 430 provides clockwise energization signals to the input terminal of driver 436 which are directed to the motor drive of left eye battery 14 through line 442. Line 431 provides a counter-clockwise drive to the left battery 14 motor through line 433. Motor 100 of right eye battery 12 is energized in a clockwise sense from line 432 directed to driver 438 which, in turn, provides energization along line 444 and counter-clockwise energization is provided to motor 100 from along line 433, driver 439 and line 445.

Returning to FIG. 12B, it may be noted that the write terminal, $\overline{WR}$, and P22 terminal of microcomputer 340 are coupled to a logic network including three NAND gates 448–450 and inverter 451 to provide a write enabling signal, W0, at line 452. This high logic level signal, W0, occurs in the presence of a low logic signal at the $\overline{WR}$ and P22 terminals of microcomputer 340. Microcomputer 340 receives about a 6 Hz oscillatory clock input signal from oscillator network 454 and, additionally, receives initialization inputs at its initialization $\overline{INT}$ and reset $\overline{RESET}$ terminals through an initialization network 456.

Since certain changes may be made in the above apparatus without departing from the scope of the invention herein involved, it is intended that all matter contained in the above description or shown in the accompanying drawings shall be interpreted as illustrative and not in a limiting sense. A machine code listing of instructions for use with the circuit of FIGS. 12A and 12B is as follows:

| 2000 | 23 | 7C | 14 | 45 | AC | 14 | 49 | FC | 03 | 4C | F6 | 00 | FC | 14 | 5E | 14 |
|------|----|----|----|----|----|----|----|----|----|----|----|----|----|----|----|----|
| 2010 | 77 | 1A | 4D | 23 | BC | 14 | 45 | AE | 14 | 49 | FE | 03 | 4C | F6 | 13 | 34 |
| 2020 | 02 | 23 | DC | 14 | 45 | AC | 14 | 49 | FC | 03 | 4C | F6 | 21 | FC | 14 | 5E |
| 2030 | 14 | A3 | 14 | 5A | 23 | EC | 14 | 45 | AE | 14 | 49 | FE | 03 | 4C | F6 | 34 |
| 2040 | 34 | 39 | 04 | 00 | 00 | 3A | 09 | E3 | 93 | 23 | FC | 3A | 93 | FD | 36 | 51 |

-continued

| | | | | | | | | | | | | | | |
|---|---|---|---|---|---|---|---|---|---|---|---|---|---|---|
| 2050 | 93 | 03 | 2D | AD | 03 | 4C | E6 | 59 | AD | 93 | FD | 56 | 51 | 93 | AD | 27 |
| 2060 | AA | AB | FC | 03 | 9C | F2 | 6A | 1A | 04 | 63 | 03 | 64 | 03 | F6 | F2 | 73 |
| 2070 | 1B | 04 | 6C | 03 | 0A | AC | 93 | 23 | F8 | 3A | FA | 96 | 7F | 23 | 0F | 03 |
| 2080 | A0 | 37 | 91 | 14 | CF | FB | 4A | 96 | 8D | 23 | 0F | 04 | 8E | FB | 03 | C0 |
| 2090 | 37 | 91 | 14 | CF | FC | 03 | E0 | 37 | 91 | 14 | CF | 23 | 8F | 37 | A1 | 23 |
| 20A0 | FC | 3A | 93 | 23 | F8 | 3A | FA | 96 | AB | 23 | 0F | 03 | 20 | 37 | 91 | 14 |
| 20B0 | CF | FB | 4A | 96 | B9 | 23 | 0F | 04 | BA | FB | 03 | 40 | 37 | 91 | 14 | CF |
| 20C0 | FC | 03 | 60 | 37 | 91 | 14 | CF | 23 | 8F | 37 | 91 | 23 | FC | 3A | 93 | B9 |
| 20D0 | 7F | E9 | D1 | 93 | 00 | 00 | 00 | 00 | 00 | 00 | 00 | 00 | 00 | 00 | 00 | 00 |
| 20E0 | 00 | 00 | 00 | 00 | 00 | 00 | 00 | 00 | 00 | 00 | 00 | 00 | 00 | 00 | 00 | 00 |
| 20F0 | 00 | 00 | 00 | 00 | 00 | 00 | 00 | 00 | 00 | 00 | 00 | 00 | 00 | 00 | 00 | 00 |
| 2100 | 00 | 00 | FD | C6 | 12 | FE | C6 | 17 | FE | 37 | 17 | 6D | C6 | 34 | F6 | 1D |
| 2110 | 24 | 29 | FE | C6 | 34 | 24 | 29 | FD | C6 | 34 | 24 | 1D | 00 | 34 | 7D | F6 |
| 2120 | 2D | 23 | 30 | 5F | 03 | 80 | 24 | 6C | 00 | 34 | 84 | F6 | 21 | 23 | 30 | 5F |
| 2130 | 03 | 40 | 24 | 6C | 23 | 30 | 5F | 24 | 6C | FD | C6 | 49 | FE | C6 | 4E | FE |
| 2140 | 37 | 17 | 6D | C6 | 69 | F6 | 53 | 24 | 5E | FE | C6 | 69 | 24 | 5E | FD | C6 |
| 2150 | 69 | 24 | 53 | 34 | 7D | F6 | 62 | 23 | C0 | 5F | 03 | 20 | 24 | 6C | 34 | 84 |
| 2160 | F6 | 57 | 23 | C0 | 5F | 03 | 10 | 24 | 6C | 23 | C0 | 5F | AF | 39 | 23 | F8 |
| 2170 | 3A | 23 | 9F | 37 | 91 | 23 | 8F | 37 | 91 | 23 | FC | 3A | 93 | FE | 37 | 17 |
| 2180 | 6D | 03 | A6 | 83 | FD | 37 | 17 | 6E | 03 | A6 | 83 | 00 | 00 | 00 | 00 | 00 |
| 2190 | 00 | 00 | 00 | 11 | 00 | 11 | 11 | 11 | 00 | 00 | 00 | 00 | 00 | 00 | 00 | 00 |
| 21A0 | 00 | 00 | 00 | 11 | 00 | 11 | 00 | 11 | 00 | 00 | 00 | 00 | 00 | 00 | 00 | 00 |
| 21B0 | 00 | 00 | 00 | 11 | 00 | 11 | 00 | 11 | 00 | 00 | 00 | 00 | 00 | 00 | 00 | 00 |
| 21C0 | 00 | 00 | 00 | 11 | 00 | 11 | 11 | 11 | 11 | 00 | 00 | 00 | 00 | 00 | 00 | 00 |
| 21D0 | 00 | 00 | 00 | 11 | 00 | 11 | 00 | 00 | 11 | 00 | 00 | 00 | 00 | 00 | 00 | 00 |
| 21E0 | 00 | 00 | 00 | 00 | 00 | 11 | 00 | 00 | 11 | 00 | 00 | 00 | 00 | 00 | 00 | 00 |
| 21F0 | 00 | 00 | 00 | 00 | 00 | 11 | 11 | 11 | 11 | 11 | 11 | 11 | 11 | 00 | 00 | 00 |
| 2200 | 11 | 11 | 11 | 11 | 00 | 00 | 00 | 00 | 00 | 11 | 00 | 00 | 11 | 00 | 00 | 00 |
| 2210 | 11 | 00 | 00 | 11 | 00 | 00 | 00 | 00 | 00 | 11 | 00 | 00 | 11 | 00 | 00 | 00 |
| 2220 | 11 | 00 | 00 | 00 | 00 | 00 | 00 | 00 | 00 | 11 | 11 | 11 | 11 | 00 | 00 | 00 |
| 2230 | 11 | 00 | 00 | 00 | 00 | 00 | 00 | 00 | 00 | 11 | 00 | 00 | 11 | 00 | 00 | 00 |
| 2240 | 11 | 00 | 11 | 11 | 11 | 00 | 00 | 00 | 00 | 11 | 00 | 00 | 11 | 00 | 00 | 00 |
| 2250 | 11 | 00 | 00 | 11 | 00 | 00 | 00 | 00 | 00 | 11 | 00 | 00 | 11 | 00 | 00 | 00 |
| 2260 | 11 | 11 | 11 | 11 | 00 | 11 | 11 | 11 | 11 | 00 | 00 | 00 | 00 | 00 | 00 | 00 |
| 2270 | 00 | 00 | 00 | 00 | 00 | 11 | 00 | 00 | 00 | 00 | 00 | 00 | 00 | 00 | 00 | 00 |
| 2280 | 00 | 00 | 00 | 00 | 00 | 11 | 00 | 00 | 00 | 11 | 11 | 11 | 11 | 00 | 00 | 00 |
| 2290 | 00 | 00 | 00 | 00 | 00 | 11 | 11 | 11 | 00 | 00 | 00 | 11 | 00 | 00 | 00 | 00 |
| 22A0 | 00 | 00 | 00 | 00 | 00 | 11 | 00 | 00 | 00 | 11 | 00 | 00 | 00 | 00 | 00 | 00 |
| 22B0 | 00 | 00 | 00 | 00 | 00 | 11 | 00 | 00 | 00 | 11 | 00 | 00 | 00 | 00 | 00 | 00 |
| 22C0 | 00 | 00 | 00 | 00 | 00 | 11 | 00 | 00 | 00 | 11 | 00 | 11 | 11 | 11 | 00 | 00 |
| 22D0 | 00 | 00 | 00 | 00 | 00 | 00 | 00 | 00 | 00 | 11 | 00 | 00 | 11 | 00 | 00 | 00 |
| 22E0 | 00 | 00 | 00 | 00 | 00 | 00 | 00 | 00 | 00 | 11 | 11 | 11 | 11 | 00 | 00 | 00 |
| 22F0 | 00 | 00 | 00 | 00 | 00 | 00 | 00 | 00 | 00 | 00 | 00 | 00 | 00 | 00 | 00 | 00 |
| 2300 | 00 | 01 | 03 | 02 | 07 | 06 | 04 | 05 | 0F | 0E | 0C | 0D | 0B | 09 | 0B | 0A |
| 2310 | 1F | 1E | 1C | 1D | 18 | 19 | 1B | 1A | 10 | 11 | 13 | 12 | 17 | 16 | 14 | 15 |
| 2320 | 3F | 3E | 3C | 3D | 38 | 39 | 3B | 3A | 30 | 31 | 33 | 32 | 37 | 36 | 34 | 35 |
| 2330 | 20 | 21 | 23 | 22 | 27 | 26 | 24 | 25 | 2F | 2E | 2C | 2D | 28 | 29 | 2B | 2A |
| 2340 | 7F | 7E | 7C | 7D | 78 | 79 | 7B | 7A | 70 | 71 | 73 | 72 | 77 | 76 | 74 | 75 |
| 2350 | 60 | 61 | 63 | 62 | 67 | 66 | 64 | 65 | 6F | 6E | 6C | 6D | 68 | 69 | 6B | 6A |
| 2360 | 40 | 41 | 43 | 42 | 47 | 46 | 44 | 45 | 4F | 4E | 4C | 4D | 48 | 49 | 4B | 4A |
| 2370 | 5F | 5E | 5C | 5D | 58 | 59 | 5B | 5A | 50 | 51 | 53 | 52 | 57 | 56 | 54 | 55 |
| 2380 | FF | FE | FC | FD | F8 | F9 | FB | FA | F0 | F1 | F3 | F2 | F7 | F6 | F4 | F5 |
| 2390 | E0 | E1 | E3 | E2 | E7 | E6 | E4 | E5 | EF | EE | EC | ED | E8 | E9 | EB | EA |
| 23A0 | C0 | C1 | C3 | C2 | C7 | C6 | C4 | C5 | CF | CE | CC | CD | C8 | C9 | CB | CA |
| 23B0 | DF | DE | DC | DD | D8 | D9 | D8 | DA | D0 | D1 | D3 | D2 | D7 | D6 | D4 | D5 |
| 23C0 | 80 | 81 | 83 | 82 | 87 | 86 | 84 | 85 | 8F | 8E | 8C | 8D | 88 | 89 | 8B | 8A |
| 23D0 | 9F | 9E | 9C | 9D | 98 | 99 | 9B | 9A | 90 | 91 | 93 | 92 | 97 | 96 | 94 | 95 |
| 23E0 | BF | BE | BC | BD | B8 | B9 | BB | BA | B0 | B1 | B3 | B2 | B7 | B6 | B4 | B5 |
| 23F0 | A0 | A1 | A3 | A2 | A7 | A6 | A4 | A5 | AF | AE | AC | AD | A8 | A9 | AB | AA |

I claim:

1. A refractor, comprising:

a housing having a patient eye position for viewing along a sight axis extensible therethrough;

a cylinder lens assembly including a plurality of rotatably movable cylinder lens components;

means for positioning select said cylinder lens components into an aligned orientation with said sight axis;

hand manipular axis control means engageable with a positioned said cylinder lens component for effecting the rotation to a select cylinder axis orientation;

first position absolute encoding means responsive to said axis control means positions for deriving a unique first position signal corresponding with the instantaneous said cylinder axis orientation of said positioned cylinder lens;

a cross-cylinder assembly operative in axis and power modes mounted upon said housing and having cross-cylinder lens means with a select power axis, rotatable lens mount means supporting said cross-cylinder lens means and movable to position said cross-cylinder lens means in alignment with said sight axis, motor means having an output coupled in driving relationship with said rotatable lens mount means and energizable in response to a drive signal to effect the rotation thereof;

second position absolute encoding means responsive to the instantaneous rotational orientation of said lens mount means for deriving a unique second position signal corresponding therewith;

digital readout means responsive to a digital input signal for displaying a numeric value corresponding therewith; and control circuit means responsive to said first position signal for deriving said digital input signal to effect said digital readout means display, responsive to said first position signal and second position signal in the presence of said axis mode condition for deriving a said drive signal effecting the driven movement of said lens mount means positioning said cross-cylinder lens means select power axis in an orientation displaced 45° from said select cylinder axis orientation, and responsive to said power mode condition for deriving a drive signal effecting the driven movement of said lens mount means positioning said cross-cylinder lens means select power axis in alignment with said select cylinder axis orientation.

2. The refractor of claim 1 in which:

said first position encoding means comprises a first code carrier mounted for movement in response to said axis control means rotation, and first readout means responsive to said first code carrier for deriving said first position signal; and said second position encoding means comprises a second code carrier mounted for movement in response to the movement of said lens mount means, and second readout means responsive to said second code carrier for deriving said second position signal.

3. The refractor of claim 2 in which said first and second code carriers are annular disks structured to carry respective first and second cyclical position codes.

4. The refractor of claim 3 in which:

each said first and second code carrier disk includes a transparent supportive substrate having said code formed thereon as discrete optically identifiable regions within message sectors of about one degree extent; and said first and second readout means comprise a source of illumination located to illuminate a said message sector positioned adjacent thereto and an array of photo detectors positioned oppositely from said source and responsive to said illumination as selectively affected by said regions to derive said respective first and second positions signals as multibit characterized signals.

5. The refractor of claim 1 in which said cross-cylinder assembly motor means is a bi-directional PM motor the said output of which is coupled in driving relationship with worm drive means, and said rotatable lens mount includes an annular, outwardly disposed gear fixed in driving relationship thereto and positioned in driven relationship with said worm drive means.

6. The refractor of claim 1 including mode display means mounted upon said housing for displaying an illuminated, visually perceptible axis mode symbol in the presence of said axis mode and for displaying an illuminated, visually perceptible power mode symbol in the presence of said power mode.

7. A refractor, comprising:

a housing having a patient eye position for viewing along a sight axis extensible therethrough;

a cylinder lens assembly including a plurality of rotatably movable cylinder lens components;

means for positioning select said cylinder lens components into an aligned orientation with said sight axis;

hand manipular axis control means engageable with a positioned said cylinder lens component for effecting the rotation thereof to a select cylinder axis orientation;

a first code carrier mounted for movement with said hand manipular axis control means;

first readout means responsive to said first code carrier for deriving a unique first position signal corresponding substantially with the instantaneous said cylinder axis orientation of said positioned cylinder lens;

a cross-cylinder assembly mounted upon said housing including a cross-cylinder lens having mutually perpendicular power axes, a rotatable lens mount selectively positionable into an aligned orientation with said sight axis, a flip mount supporting said cross-cylinder upon said rotatable lens mount for pivotal movement about a flip disposed intermediate said perpendicular power axes, motor means having an output coupled in driving relationship with said rotatable lens mount and energizable in response to a drive signal to effect the rotation thereof;

a second code carrier mounted for movement with said rotatable lens mount;

second readout means for deriving a unique second position signal corresponding substantially with the instantaneous position of said cross-cylinder lens power axes;

digital readout means responsive to a digital input signal for displaying a numeric value corresponding therewith visually perceptible in the presence of low ambient illumination;

mode switch means selectively actuable to provide an axis mode condition and a power mode condition; and control circuit means responsive to said first position signal for deriving said digital input signal to effect said digital readout means display, responsive to said first position signal and said second position signal in the presence of said axis mode condition for deriving a said drive signal until said cross-cylinder lens flip axis is located parallel with said positioned cylinder lens component cylinder axis, and responsive to said first position signal and said second position signal in the presence of said power mode condition for deriving a said drive signal until a selected said cross-cylinder lens power axis is located parallel with said positioned cylinder lens component cylinder axis.

8. The refractor of claim 7 in which said first and second code carriers incorporate cyclical position codes readable by respective said first and second readout means.

9. The refractor of claim 7 in which:

said first and second code carriers are annular disks respectively supporting substantially identical first and second optically readable cyclical position codes; and said first and second readout means are optically responsive to respective said first and second position codes.

10. The refractor of claim 9 in which:

each said first and second code carrier disk includes a transparent supportive substrate having said code formed thereon as discrete optically identifiable regions within message sectors of about one degree extent; and said first and second readout means comprise a source of radiation located to impinge upon a said message sector positioned adjacent thereto and an array of photo detectors positioned oppositely from said source and responsive to said radiation as selectively affected by said regions to derive said respective first and second position signals as multi-bit characterized signals.

11. The refractor of claim 10 in which said first and second optically readable position codes are Gray codes.

12. The refractor of claim 11 in which said control circuit means includes memory means carrying look-up data for converting said first and second position signals to binary coded signals, and said control means is responsive to said first position signal to derive a corresponding binary signal from said memory means and derives therefrom said binary digital input signal as a binary coded decimal signal.

13. The refractor of claim 7 in which said cross-cylinder assembly motor means is a bi-directional PM motor the said output of which is coupled in driving relationship with worm drive means, and said rotatable lens mount includes an annular, outwardly disposed gear fixed in driving relationship thereto and positioned in driven relationship with said worm drive means.

14. The refractor of claim 7 including mode display means mounted upon said housing and responsive when said mode switch means provides said axis mode condition to display an illuminated symbol A, and responsive when said mode switch means provides said power mode condition to display an illuminated symbol P.

15. A refractor comprising:
a battery having a patient eye position aligned along a sight axis extensible therethrough;
a cylinder lens assembly including a plurality of rotatable cylinder lenses each having a cylinder axis;
means for positioning a selected cylinder lens in alignment with said sight axis;
axis control means rotatable to select positions for setting the cylinder axis of a said selected cylinder lens;
first position absolute encoding means mounted upon said battery, responsive to said axis control means positions for deriving a unique first position signal for each said cylindrical axis setting;
a cross-cylinder assembly mounted upon said battery and having cross-cylinder lens means with a select power axis, rotatable lens mount means supporting said cross-cylinder lens means, a turret supporting said lens mount and movable to position said cross-cylinder lens in alignment with said sight axis, motor means mounted upon said turret, having an output coupled in driving relationship with said rotatable lens mount means and energizable in response to a drive signal to effect the rotation thereof;
second position absolute encoding means mounted upon said turret, responsive to the rotational orientation of said lens mount means for deriving a unique second position signal;
mode switch means for providing an axis mode condition and a power mode condition; and
control circuit means responsive to said first position signal and said second position signal in the presence of said axis mode condition for deriving a said drive signal effecting the driven movement of said lens mount means positioning said cross-cylinder lens means select power axis in an orientation displaced 45° from said cylinder axis, and responsive to said first position signal and said second position signal in the presence of said power mode condition for deriving a drive signal effecting the driven movement of said lens mount means positioning said cross-cylinder lens means select power axis in alignment with said cylinder axis.

16. The refractor of claim 15 in which:
said first position absolute encoding means comprises a first code carrier mounted for movement in response to said axis control means rotation, and first readout means responsive to said first code carrier for deriving said first position signal; and
said second position absolute encoding means comprises a second code carrier mounted for movement in response to the movement of said lens mount means, and second readout means responsive to said second code carrier for deriving said second position signal.

17. The refractor of claim 16 in which said first and second code carriers are annular disks structured to carry respective first and second cyclical position codes.

18. The refractor of claim 17 in which:
each said first and second code carrier disk includes a transparent supportive substrate having said code formed thereon as discrete optically identifiable regions within message sectors of about one degree extent; and
said first and second readout means comprise a source of radiation located to impinge upon a said message sector positioned adjacent thereto and an array of photo detectors positioned oppositely from said source and responsive to said radiation as selectively affected by said regions to derive said respective first and second position signals as multi-bit characterized signals.

19. The refractor of claim 15 in which said cross-cylinder assembly motor means is a bi-directional PM motor the said output of which is coupled in driving relationship with worm drive means, and said rotatable lens mount includes an annular, outwardly disposed gear fixed in driving relationship thereto and positioned in driven relationship with said worm drive means.

20. The refractor of claim 15 including:
digital readout means responsive to a digital input signal for displaying a numeric value corresponding therewith visually perceptible in the presence of low ambient illumination; and
said control circuit means is responsive to said first position signal for deriving said digital input signal to effect said digital readout means display.

* * * * *